(12) United States Patent
Serizawa et al.

(10) Patent No.: US 11,939,322 B2
(45) Date of Patent: Mar. 26, 2024

(54) METHOD FOR PRODUCING TETRACYCLIC COMPOUND

(71) Applicant: Chugai Seiyaku Kabushiki Kaisha, Tokyo (JP)

(72) Inventors: Hiroki Serizawa, Tokyo (JP); Akira Kawase, Tokyo (JP); Hiroshi Fukuda, Tokyo (JP); Naoto Hama, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 507 days.

(21) Appl. No.: 17/271,437

(22) PCT Filed: Sep. 3, 2019

(86) PCT No.: PCT/JP2019/034543
§ 371 (c)(1),
(2) Date: Feb. 25, 2021

(87) PCT Pub. No.: WO2020/050241
PCT Pub. Date: Mar. 12, 2020

(65) Prior Publication Data
US 2022/0372025 A1    Nov. 24, 2022

(30) Foreign Application Priority Data
Sep. 4, 2018 (JP) .................. 2018-165313

(51) Int. Cl.
*C07D 413/04* (2006.01)
(52) U.S. Cl.
CPC .................. *C07D 413/04* (2013.01)
(58) Field of Classification Search
CPC .................. C07D 413/04
USPC .................. 514/229.5
See application file for complete search history.

(56) References Cited

U.S. PATENT DOCUMENTS

| | | |
|---|---|---|
| 5,721,267 A | 2/1998 | Broka |
| 5,936,084 A | 8/1999 | Jirousek et al. |
| 7,060,721 B1 | 6/2006 | Oku et al. |
| 9,126,931 B2 | 9/2015 | Kinoshita et al. |
| 9,365,514 B2 | 6/2016 | Furumoto et al. |
| 9,440,922 B2 | 9/2016 | Kinoshita et al. |
| 9,714,229 B2 | 7/2017 | Tanaka et al. |
| 10,344,014 B2 | 7/2019 | Shiraki et al. |
| 2004/0072890 A1 | 4/2004 | Munro et al. |
| 2005/0107364 A1 | 5/2005 | Hutchinson et al. |
| 2006/0063790 A1 | 3/2006 | Gillman et al. |
| 2007/0031907 A1 | 2/2007 | Pinna et al. |
| 2007/0099893 A1 | 5/2007 | Boyd et al. |
| 2007/0249653 A1 | 10/2007 | Jagtap et al. |
| 2008/0058320 A1 | 3/2008 | Herold et al. |
| 2008/0095838 A1 | 4/2008 | Abou Chacra-Vernet |
| 2008/0242644 A1 | 10/2008 | Watson |
| 2008/0262021 A1 | 10/2008 | Capraro et al. |
| 2009/0221555 A1 | 9/2009 | Ahmed et al. |
| 2010/0099658 A1 | 4/2010 | Kondoh et al. |
| 2012/0083488 A1 | 4/2012 | Kinoshita et al. |
| 2013/0143877 A1 | 6/2013 | Furumoto et al. |

(Continued)

FOREIGN PATENT DOCUMENTS

| | | |
|---|---|---|
| CN | 1335837 A | 2/2002 |
| CN | 1902200 A | 1/2007 |

(Continued)

OTHER PUBLICATIONS

U.S. Appl. No. 16/862,125, filed Apr. 29, 2020, Kinoshita et al.
U.S. Appl. No. 17/019,896, filed Sep. 14, 2020, Shiraki et al.
U.S. Appl. No. 17/255,707, filed Dec. 23, 2020, Kitayama et al.
Asche et al., "Synthesis, antitumour activity and structure-activity relationships of 5H-benzo[b]carbazoles," Bioorganic & Medicinal Chemistry, 2005, 13:819-837.

(Continued)

*Primary Examiner* — Kahsay Habte
(74) *Attorney, Agent, or Firm* — Foley & Lardner LLP

(57) ABSTRACT

This invention relates to a method for manufacturing 9-ethyl-6,6-dimethyl-8-[4-(morpholin-4-yl)piperidin-1-yl]-11-oxo-6,11-dihydro-5H-benzo[b]carbazole-3-carbonitrile, and is industrially preferable, allowing an objective substance to be obtained in high yield more safely and easily than the conventional method.

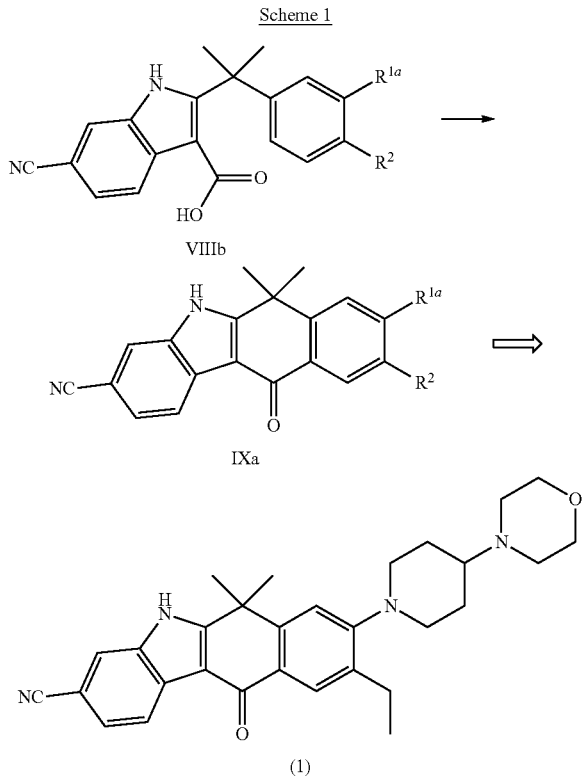

13 Claims, 7 Drawing Sheets

(56) References Cited

U.S. PATENT DOCUMENTS

| | | |
|---|---|---|
| 2015/0150845 A1 | 6/2015 | Kinoshita et al. |
| 2015/0272958 A1 | 10/2015 | Kodama et al. |
| 2016/0257667 A1 | 9/2016 | Xu |
| 2016/0317494 A1 | 11/2016 | Furumoto et al. |
| 2016/0340308 A1 | 11/2016 | Kinoshita et al. |
| 2017/0035773 A1 | 2/2017 | Tomimatsu et al. |
| 2017/0081306 A1 | 3/2017 | Tanaka et al. |
| 2017/0119781 A1 | 5/2017 | Meier et al. |
| 2017/0217927 A1 | 8/2017 | Shiraki et al. |
| 2017/0247352 A1 | 8/2017 | Xu |
| 2019/0284163 A1 | 9/2019 | Shiraki et al. |
| 2020/0017442 A1 | 1/2020 | Kinoshita et al. |
| 2020/0038407 A1 | 2/2020 | Tomimatsu et al. |
| 2020/0246349 A1 | 8/2020 | Kodama et al. |
| 2021/0052550 A1 | 2/2021 | Furumoto et al. |

FOREIGN PATENT DOCUMENTS

| | | |
|---|---|---|
| CN | 1976903 A | 6/2007 |
| CN | 106928184 A | 7/2017 |
| CN | 106928185 A | 7/2017 |
| CN | 107033124 A | 8/2017 |
| EA | 001450 B1 | 4/2001 |
| EP | 2 253 318 | 11/2010 |
| EP | 2 441 753 A1 | 4/2012 |
| JP | 08-092090 A | 4/1996 |
| JP | 4588121 B1 | 11/2010 |
| JP | 4918630 B1 | 4/2012 |
| JP | 2012-126711 A | 7/2012 |
| JP | 5006987 B2 | 7/2012 |
| JP | 5859712 B1 | 2/2016 |
| RU | 2162089 C2 | 1/2001 |
| WO | WO-00/69856 A1 | 11/2000 |
| WO | WO-2004/080980 A1 | 9/2004 |
| WO | WO-2005/009389 A2 | 2/2005 |
| WO | WO-2005/092062 A2 | 10/2005 |
| WO | WO-2005/097765 A1 | 10/2005 |
| WO | WO-2006/021884 A2 | 3/2006 |
| WO | WO-2007/023310 A2 | 3/2007 |
| WO | WO-2007/056497 A1 | 5/2007 |
| WO | WO-2007/130468 A2 | 11/2007 |
| WO | WO-2008/021369 A2 | 2/2008 |
| WO | WO-2008/051547 A1 | 5/2008 |
| WO | WO-2008/130951 A1 | 10/2008 |
| WO | WO-2009/008371 A1 | 1/2009 |
| WO | WO-2009/013126 A1 | 1/2009 |
| WO | WO-2009/073620 A2 | 6/2009 |
| WO | WO-2010/128324 A1 | 11/2010 |
| WO | WO-2010/142423 A2 | 12/2010 |
| WO | WO-2010/142685 A1 | 12/2010 |
| WO | WO-2017/073706 A1 | 5/2017 |

OTHER PUBLICATIONS

Bernardo et al., "Synthesis, Electrochemistry, and Bioactivity of the Cyanobacterial Calothrixins and Related Quinones," J. Med. Chem., 2004, 47:4958-4963.

Boogaard et al., "Ring D Modifications of Ellipticine. Part 2. Chlorination of Ellipticine via its N-oxide and Synthesis and Selective Oxidation of 5,6,11-Trimethyl-5H-Benzo[b]Carbazole," Tetrahedron, 1994, 50(16):4811-4828.

Bunz, F., "Chapter 1, The Genetic Basis of Cancer," Principles of Cancer Genetics, 2008, 1-47.

CAS RN 100863-39-6, STN Entry Date Mar. 15, 1986.
CAS RN 222318-66-3, STN Entry Date May 7, 1999.
CAS RN 24716-14-1, STN Entry Date Nov. 16, 1984.
CAS RN 36263-63-5, STN Entry Date Nov. 16, 1984.
CAS RN 4355-38-8, STN Entry Date Nov. 16, 1984.
CAS RN 6008-29-3, STN Entry Date Nov. 16, 1984.
CAS RN 61492-49-7, STN Entry Date Nov. 16, 1984.
CAS RN 74205-47-3, STN Entry Date Nov. 16, 1984.
CAS RN 89579-57-7, STN Entry Date Nov. 16, 1984.
CAS RN 93257-39-7, STN Entry Date Dec. 18, 1984.

Chang et al., "Polymethacrylates," Handbook of Pharmaceutical Excipients, Rowe et al., Eds., 2009, 6th Ed., 525-533.

Chen et al., "Oncogenic mutations of ALK kinase in neuroblastoma," Nature, Oct. 16, 2008, 455:971-974, and Methods page.

Cools et al., "Identification of Novel Fusion Partners of ALK, the Anaplastic Lymphoma Kinase, in Anaplastic Large-Cell Lymphoma and Inflammatory Myofibroblastic Tumor," Genes, Chromosomes & Cancer, 2002, 34:354-362.

Database Accession No. 1:1259(XP55784247), RN 826-55-1, 1907, one page.

Database Accession No. 27:43772 (XP55784257), RN 37828-19-6 CA, 1933, one page.

Database Accession No. 28:22560 (XP55784253), RN 77-55-4, 1934, one page.

Database Accession No. 28:22560 (XP55784254), RN 1135-67-7, 1934, one page.

Database Accession No. 41:3570(XP55784249), RN 6120-95-2, 1946, one page.

Davies, Peter, "Oral Solid Dosage Forms," Drugs and the Pharmaceutical Sciences, Pharmaceutical Preformulation and Formulation, Mark Gibson, Ed., 2009, 2nd Edition, 199:367-430.

Defendant Fresenius Kabi USA, LLC's Initial Invalidity Contentions, filed Oct. 9, 2020 in C.A. No. 20-394 (RGA), *Hoffmann-LaRoche, Inc., Chugai Pharmaceutical Co., Ltd.,* and *Genentech, Inc.* (Plaintiffs and Counterclaim Defendants) v. *Fresenius Kabi USA, LLC* (Defendant and Counterclaim Plantiff), 112 pages.

Druker et al., "Section 1: Chronic Myelogenous Leukemia," Cancer: Principles & Practice of Oncology, 7th Edition (DeVita et al., Eds.), 2121.

Faderl et al., "Section 3: Myelodysplastic Syndromes," Cancer: Principles & Practice of Oncology, 7th Edition (DeVita et al., Eds.), 2144.

Fine et al., "Section 2: Neoplasms of the Central Nervous System," Cancer: Principles & Practice of Oncology, 7th Edition (DeVita et al., Eds.), 1834-1887.

Fischer et al., "A Ki-1(CD30)-Positive Human Cell Line (Karpas 299) Established From a High-Grade Non-Hodgkin's Lymphoma, Showing a 2;5 Translocation and Rearrangement of the T-Cell Receptor β-Chain Gene," Blood, Jul. 1988, 72(1):234-240.

Gadgeel et al., "A Phase 1 Dose Escalation Study of a New ALK Inhibitor, CH5424802/RO5424802, in ALK Non-Small Cell Lung Cancer (NSCLC) Patients who have Failed Crizotinib (AF-002JG/NP28761, NCT01588028)," Journal of Thoracic Oncology, Nov. 2013, 8(2):S199, Abstract O16.06.

Gadgeel et al., "Safety and activity of alectinib against systemic disease and brain metastases in patients with crizotinib-resistant ALK-rearranged non-small-cell lung cancer (AF-002JG): results from the dose-finding portion of a phase 1/2 study," Lancet Oncology, 2014, 15:1119-1128.

Galkin et al., "Identification of NVP-TAE684, a potent, selective and efficacious inhibitor of NPM-ALK," PNAS, Jan. 2, 2007, 104(1):270-275.

Galkin et al., "Identification of NVP-TAE684, a potent, selective and efficacious inhibitor of NPM-ALK," PNAS, Jan. 2, 2007, 104(1):270-275 (and Corrections published in PNAS, Feb. 6, 2007, 104(6):2024-2025).

Garbett et al., "Extending Nature's Leads: The Anticancer Agent Ellipticine," Curr. Med. Chem.—Anti-Cancer Agents, 2004, 4:149-172.

George et al., "Activating mutations in ALK provide a therapeutic target in neuroblastoma," Nature, 2008, 455:975-978.

Girouard et al., "Neurovascular coupling in the normal brain and in hypertension, stroke, and Alzheimer disease," Journal of Applied Physiology, 2006, 100:328-335.

Glick et al., "Treatment with atypical antipsychotics: new indications and new populations," Journal of Psychiatric Research, 2001, 35:187-191.

Goel et al., "Mice transgenic for BRAF V600E demonstrate phenotype affecting melanocyte and neural lineages," Proceedings of the American Association for Cancer Research, Apr. 2006, 47:#273.

(56) References Cited

OTHER PUBLICATIONS

Goodman & Gilman's, Chemotherapy of Neoplastic Diseases, The Pharmacological Basis of Therapeutics, Brunton et al., Eds., 2008, 11th Ed., 853-908.
Griffin et al., "Recurrent Involvement of 2p23 in Inflammatory Myofibroblastic Tumors," Cancer Research, Jun. 15, 1999, 59:2776-2780.
Gunby et al., "Structural Insights into the ATP Binding Pocket of the Anaplastic Lymphoma Kinase by Site-Directed Mutagenesis, Inhibitor Binding Analysis, and Homology Modeling," J. Med. Chem., 2006, 49:5759-5768.
Herbst et al., "ALK Gene Products in Anaplastic Large Cell Lymphomas and Hodgkin's Disease," Blood, Sep. 1, 1995, 86(5):1694-1700.
Hida et al., "Pharmacologic study (JP28927) of alectinib in Japanese patients with ALK non-small-cell lung cancer with or without prior crizotinib therapy," Cancer Science, 2016, 107:1642-1646.
Hooton, J.C., "Carboxymethylcellulose Calcium," Handbook of Pharmaceutical Excipients, Rowe et al., Eds., 6th Ed., 2009, 117-118.
Huang et al., "An in vivo model to study human GSTP1 polymorphisms in osteosarcoma," Proceedings of the American Association for Cancer Research, Apr. 2006, 47:#271.
Hübinger et al., "CD30-mediated cell cycle arrest associated with induced expression of p21CIP1/WAF1 in the anaplastic large cell lymphoma cell line Karpas 299," Oncogene, 2001, 20:590-598.
Inoue et al., "One-year Follow-up of a Phase I/II Study of a Highly Selective ALK Inhibitor CH5424802/RO5424802 in ALK-Rearranged Advanced Non-Small Cell Lung Cancer (NSCLC)," Journal of Thoracic Oncology, Nov. 2013, 8(Supp.2):S1204, Abstract P3.11-034.
Jazii et al., "Identification of squamous cell carcinoma associated proteins by proteomics and loss of beta tropomyosin expression in esophageal cancer," World J. Gastroenterol., Nov. 28, 2006, 12(44):7104-7112.
Kabir et al., "Hydroxypropyl Cellulose," Handbook of Pharmaceutical Excipients, Rowe et al., Eds., 6th Ed., 2009, 317-322.
Kashyap et al., "Fast Disintegrating Tablet: A Boon to Pediatric and Geriatric," International Journal of Pharma Professional's Research, Apr. 2011, 2(2):318-326.
Kinoshita et al., "Design and synthesis of a highly selective, orally active and potent anaplastic lymphoma kinase inhibitor (CH5424802)," Bioorganic & Medicinal Chemistry, 2012, 20:1271-1280.
Kirsch, Gilbert H., "Heterocyclic Analogues of Carbazole Alkaloids," Current Organic Chemistry, 2001, 5:507-518.
Knoelker et al., "Transition Metal Complexes in Organic Synthesis, Part 38. First Total Synthesis of Carbazomycin G and H," Tetrahedron Letters, 1997, 38(23):4051-4054.
Kuppen et al., "Tumor structure and extracellular matrix as a possible barrier for therapeutic approaches using immune cells or adenoviruses in colorectal cancer," Histochem. Cell. Biol., 2001, 115:67-72.
Kuster, Bernhard, Ed., Kinase Inhibitors, Methods and Protocols, Methods in Molecular Biology, 2012, vol. 795, Chapter 1 by Fabbro et al., "Targeting Cancer with Small-Molecular-Weight Kinase Inhibitors.".
Kwak et al., "Anaplastic Lymphoma Kinase Inhibition in Non-Small-Cell Lung Cancer," The New England Journal of Medicine, Oct. 28, 2010, 363(18):1693-1703.
Lamant et al., "Establishment of a novel anaplastic large-cell lymphoma-cell line (COST) from a 'small-cell variant' of ALCL," Leukemia, 2004, 18:1693-1698.
Li et al., "Design and Synthesis of 5-Aryl-pyridone-carboxamides as Inhibitors of Anaplastic Lymphoma Kinase," J. Med. Chem., 2006, 49:1006-1015.
Li et al., "Development of Anaplastic Lymphoma Kinase (ALK) Small-Molecule Inhibitors for Cancer Therapy," Medicinal Research Reviews, 2008 (online Aug. 10, 2007), 23(3):372-412.
Liao, Jeffrey Jie-Lou, "Molecular Recognition of Protein Kinase Binding Pockets for Design of Potent and Selective Kinase Inhibitors," Journal of Medicinal Chemistry, Feb. 8, 2007, 50(3):409-424.
Lissoni et al., "Biotherapy with the pineal hormone melatonin plus aloe and myrrh tincture in untreatable metastatic cancer patients as an essence therapy of cancer," Cancer Therapy, 2009, 7:397-401.
Luo et al., "Principles of Cancer Therapy: Oncogene and Non-oncogene Addiction," Cell, Mar. 6, 2009, 136:823-837.
Mosse et al., "Identification of ALK as a major familial neuroblastoma predisposition gene," Nature, Oct. 16, 2008, 455:930-935, and Methods page.
Nakagawa et al., "A phase I/II study with a highly selective ALK inhibitor CH5424802/RO5424802 in ALK-positive non-small cell lung cancer (NSCLC) patients: Updated safety and efficacy results from AF-001JP," 49th Annual Meeting of the American Society of Clinical Oncology (ASCO), Chicago, IL, May 31, 2013-Jun. 4, 2013, poster, Abstract No. 8033.
Nakagawa et al., "Antitumor Activity of alectinib (CH5424802/RO5424802) for ALK-Rearranged NSCLC with or without Prior crizotinib Treatment in Bioequivalence Study," 49th Annual Meeting of the American Society of Clinical Oncology (ASCO), Chicago, IL, May 31, 2013-Jun. 4, 2013, poster, Abstract No. 8033.
National Cancer Institute, http://www.cancer.gov/, "A to Z List of Cancers," downloaded May 29, 2014, 22 pages.
O'Brien et al., "Section 2: Chronic Lymphoid Leukemias," Cancer: Principles & Practice of Oncology, 7th Edition (DeVita et al., Eds.), 2005, 2133.
O'Brien et al., "Vascular cognitive impairment," The Lancet Neurology, Feb. 2003, 2:89-98.
Ou et al., "Consistent Therapeutic Efficacy of CH5424802/RO5424802 in Brain Metastases Among Crizotinib-Refractory ALK-Positive Non-small Cell Lung Cancer (NSCLC) Patients in an Ongoing Phase I/II Study (AF-002JG/NP28761, NCT01588028)," Journal of Thoracic Oncology, Nov. 2013, 8(2):Abstract O17.07.
Pao et al., "EGF receptor gene mutations are common in lung cancers from 'never smokers' and are associated with sensitivity of tumors to gefitinib and erlotinib," PNAS, Sep. 7, 2004, 101(36):13306-13311.
Piva et al., "Ablation of oncogenic ALK is a viable therapeutic approach for anaplastic large-cell lymphomas," Blood, Jan. 2006, 107(2):689-697.
Plumb, P., "Sodium Lauryl Sulfate," Handbook of Pharmaceutical Excipients, Rowe et al., Eds., 6th Ed., 2009, 652-653.
Rosenwald et al., "t(1;2)(q21;p23) and t(2;3)(p23;q21): Two Novel Variant Translocations of the t(2;5)(p23;q35) in Anaplastic Large Cell Lymphoma," Blood, Jul. 1, 1999, 94(1):362-364.
Scheinberg et al., "Section 2: Management of Acute Leukemias," Cancer: Principles & Practice of Oncology, 7th Edition (DeVita et al., Eds.), 2005, 2088, 2092.
Seto et al., "CH5424802 (RO5424802) for patients with ALK-rearranged advanced non-small-cell lung cancer (AF-001JP study): a single-arm, open-label, phase 1-2 study," Lancet Oncology, Jun. 2013, 14:590-598.
Shah et al., "Current approaches in the treatment of Alzheimer's disease," Biomedicine & Pharmacotherapy, 2008, 62:199-207.
Shaw et al., "Targeting Anaplastic Lymphoma Kinase in Lung Cancer," Clinical Cancer Research, 2011, 17:2081-2086.
Sheridan, Robert P., "The Most Common Chemical Replacements in Drug-Like Compounds," J. Chem. Inf. Comput. Sci., 2002, 42:103-108.
Shujuan, Wang, "The new insights on the diagnosis of malignant histiocytosis," Chinese Journal of Laboratory Medicine, Jan. 30, 2005, 28(1):14-16.
Silverman, Richard B., The Organic Chemistry of Drug Design and Drug Action, Second Ed., Elsevier Academic Press, Northwestern University, Evanston, Illinois, 2004, 29-31, table 2.2.
Soda et al., "Identification of the transforming EML4-ALK fusion gene in non-small-cell lung cancer," Nature, Aug. 2, 2007, 448:561-566, and Methods page.
Soussi, Thierry, "p53 Antibodies in the Sera of Patients with Various Types of Cancer: A Review," Cancer Res., 2000, 60:1777-1788.

(56) References Cited

OTHER PUBLICATIONS

Stoica et al., "Identification of Anaplastic Lymphoma Kinase as a Receptor for the Growth Factor Pleiotrophin," J. Biol. Chem., May 18, 2001, 276(20:16772-16779.
Stoica et al., "Midkine Binds to Anaplastic Lymphoma Kinase (ALK) and Acts as a Growth Factor for Different Cell Types," J. Biol. Chem., Sep. 27, 2002, 277(39):35990-35998.
Vendome et al., "Molecular Modeling of Wild-Type and D816V c-Kit Inhibition Based on ATP-Competitive Binding of Ellipticine Derivatives to Tyrosine Kinases," J. Med. Chem., 2005, 48:6194-6201.
Wanner et al., "A convenient synthesis of 6-methylellipticine and 6-methylolivacine," Heterocycles, 1982, 19(12):2295-2300.
Wendling, Patrice, "Alectinib active in ALK-positive, crizotinib-refractory NSCLC," Chest Physician, Oct. 9, 2013, 4 pages.
Wood et al., "Lack of the t(2;5) or Other Mutations Resulting in Expression of Anaplastic Lymphoma Kinase Catalytic Domain in CD30+ Primary Cutaneous Lymphoproliferative Disorders and Hodgkin's Disease," Blood, Sep. 1, 1996, 88(5):1765-1770.
Zhao et al., "The progress of the research on anaplastic lymphoma kinase genetic abnormality of anaplastic large cell lymphoma," Foreign Medical Sciences (Section of Blood Transfusion and Heanatology), Oct. 15, 2004, 27(5):403-406.
Bilsland et al., "Behavioral and Neurochemical Alterations in Mice Deficient in Anaplastic Lymphoma Kinase Suggest Therapeutic Potential for Psychiatric Indications," Neuropsychopharmacology, 2008, 33:685-700.
Soda et al., "Identification of the transforming EML4-ALK fusion gene in non-small-cell lung cancer," Nature, Aug. 2, 2007, 448:561-567.

METHOD FOR PRODUCING TETRACYCLIC COMPOUND

CROSS-REFERENCE TO RELATED APPLICATIONS

This application is the U.S. National Stage of PCT/JP2019/034543, filed Sep. 3, 2019, which claims priority to JP 2018-165313, filed Sep. 4, 2018.

TECHNICAL FIELD

The present invention relates to a method for manufacturing a tetracyclic compound.

BACKGROUND ART

Anaplastic Lymphoma Kinase (ALK) is one of receptor tyrosine kinases belonging to the insulin receptor family (Non Patent Literature 1, and Non Patent Literature 2), and as diseases accompanied by abnormality of ALK, for example, cancer and cancer metastasis (Non Patent Literature 1: Nature, 448, 561-566, 2007, and Patent Literature 1: Japanese Patent No. 4588121), depression, cognitive dysfunction (Non Patent Literature 2: Neuropsychopharmacology, 33, pp. 685-700, 2008) are known, and an ALK inhibitor is useful as a therapeutic and prophylactic drug for such diseases.

As a compound having an ALK inhibitory action, a Compound (1) (9-ethyl-6,6-dimethyl-8-[4-(morpholin-4-yl)piperidin-1-yl]-11-oxo-6,11-dihydro-5H-benzo[b]carbazole-3-carbonitrile) has been known, and the Compound (1), a pharmaceutically acceptable salt thereof, or the like is known to be useful as an effective therapeutic and prophylactic drug for diseases associated with ALK abnormality (Patent Literature 1, Patent Literature 2: Japanese Patent No. 4918630, Patent Literature 3: Japanese Patent No. 5006987, and Patent Literature 4: Japanese Patent No. 5859712).

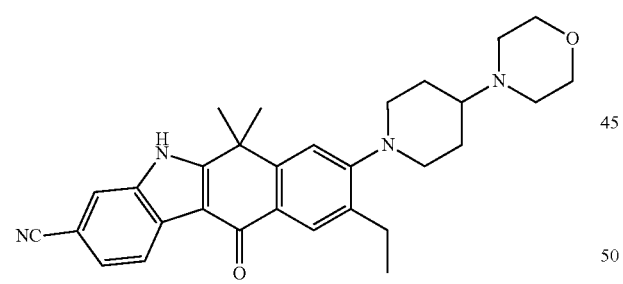

(1)

As a method for producing the Compound (1), for example, a method disclosed as the Preparation method III in Patent Literature 1 is known.

However, the preparation method of Patent Literature 1 had various difficulties, such as an impact of a used solvent on the environment, safety, and formation of by-products and regioisomers, and a further improved method has been demanded.

SUMMARY OF INVENTION

Technical Problem

An object of the present invention is to provide an industrially preferable manufacturing method by which an objective substance can be obtained in high yield more safely and easily as compared with the conventional method.

Solution to Problem

The present inventors have studied diligently for achieving the object and as a result found the following manufacturing method, by which the objective substance can be obtained with less effort by avoiding the use of a substance of very high concern as a solvent.

That is, the present invention is as follows.

[1] A method for manufacturing Compound (1):

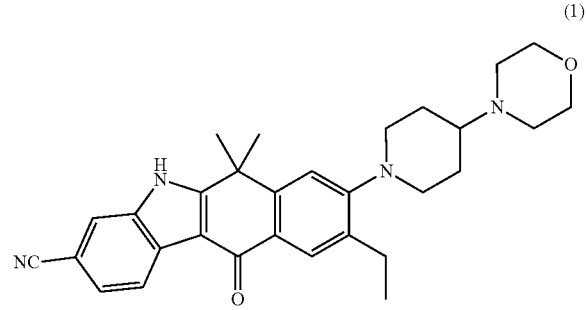 [SMILES: CCc1cc2c(cc1N1CCC(N3CCOCC3)CC1)C(C)(C)c1[nH]c3cc(C#N)ccc3c1C2=O]

(1)

a pharmaceutically acceptable salt thereof, or a solvate thereof, the method comprising a step of manufacturing a compound represented by Formula IXa:

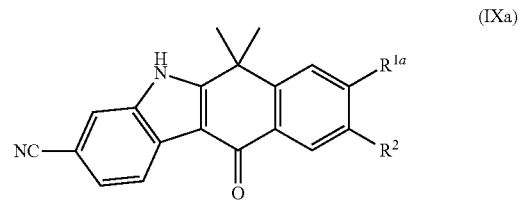

(IXa)

a pharmaceutically acceptable salt thereof, or a solvate thereof, by treating a compound represented by Formula VIIIb:

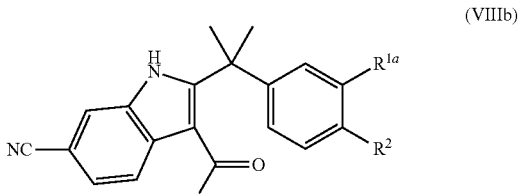

(VIIIb)

wherein $R^{1a}$ represents a leaving group, or an optionally substituted 6-membered saturated cyclic amino group; and $R^2$ represents a $C_1$-$C_6$ alkyl group, with a condensing agent in a solvent selected from dichloromethane, 1,4-dioxane, 2-methyltetrahydrofuran, 2-butanone, tert-butyl methyl ether, ethyl acetate, isopropyl acetate, dimethyl sulfoxide, tetrahydrofuran, acetone, and acetonitrile.

[1-2] The method according to [1] above, wherein Formula VIIIb refers to 6-cyano-2-[1-[4-ethyl-3-(4-morpholino-1-piperidyl)phenyl]-1-methyl-ethyl]-1H-indole-3-carboxylic acid, and Formula IXa refers to 9-ethyl-6,6-dimethyl-8-[4-(morpholin-4-yl)piperidin-1-yl]-11-oxo-6,11-dihydro-5H-benzo[b]carbazole-3-carbonitrile.

[2] The method according to [1] above, further comprising any of:

(1) Step 1a: a step of reacting a compound represented by Formula I:

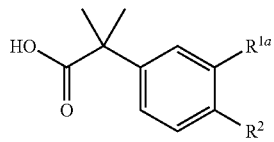

wherein $R^{1a}$ represents a leaving group, or an optionally substituted 6-membered saturated cyclic amino group; and $R^2$ represents a $C_1$-$C_6$ alkyl group, in the presence of an acid to produce a compound represented by Formula II:

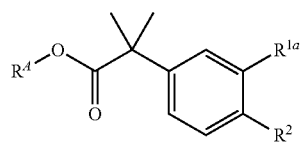

wherein $R^{1a}$ and $R^2$ are as defined above, and RA represents a $C_1$-$C_6$ alkyl group;

(2) Step 1b: a step of reacting the compound represented by Formula II with a base and AcOR$^B$ to produce a compound represented by Formula III:

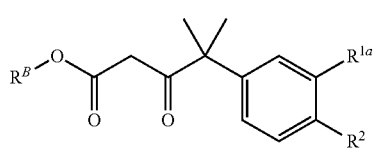

wherein $R^{1a}$ and $R^2$ are as defined above, and $R^B$ represents a $C_1$-$C_6$ alkyl group;

(3) Step 2a: a step of reacting the compound represented by Formula III with a compound represented by Formula IV and a base:

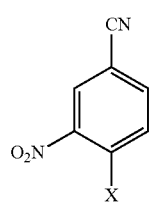

wherein X represents a leaving group, to produce a compound represented by Formula V:

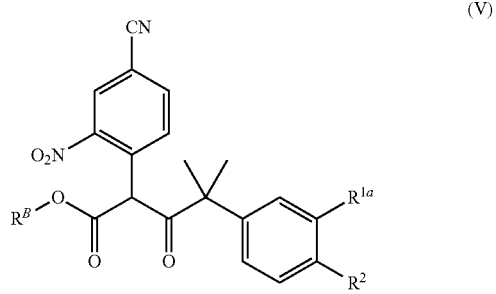

wherein $R^{1a}$, $R^2$, and $R^B$ are as defined above;

(4) Step 2b-c: a step of reacting the compound represented by Formula V with a reducing agent to produce a compound represented by Formula VI:

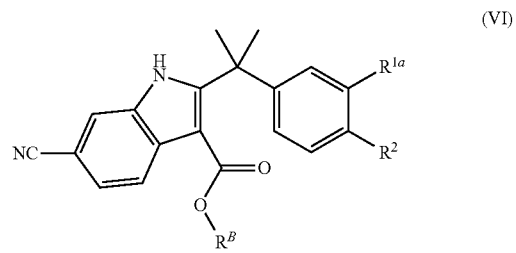

wherein $R^{1a}$, $R^2$, and $R^B$ are as defined above;

(5) Step 3: a step of reacting the compound represented by Formula VI in the presence of a palladium catalyst with an optionally substituted 6-membered saturated cyclic amine to produce a compound represented by Formula VII:

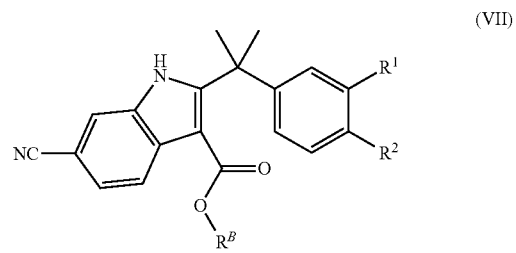

wherein $R^1$ represents an optionally substituted 6-membered saturated cyclic amino group, and $R^2$ and $R^B$ are as defined above, a pharmaceutically acceptable salt thereof, or a solvate of either of them; and (6) Step 4: a step of reacting the compound represented by Formula VII with an acid to produce a compound represented by Formula VIII:

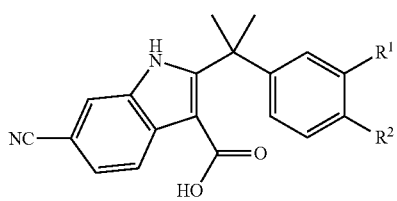

(VIII)

wherein R¹ and R² are as defined above.

[2-1] The method according to [2] above, wherein Formula I refers to 2-(4-ethyl-3-iodo-phenyl)-2-methyl-propanoic acid; Formula II refers to methyl 2-(4-ethyl-3-iodo-phenyl)-2-methyl-propanoate; Formula III refers to tert-butyl 4-(4-ethyl-3-iodo-phenyl)-4-methyl-3-oxo-pentanoate; Formula IV refers to 4-fluoro-3-nitrobenzonitrile; Formula V refers to tert-butyl 6-cyano-2-[1-(4-ethyl-3-iodo-phenyl)-1-methyl-ethyl]-1H-indole-3-carboxylate; Formula VI refers to tert-butyl 6-cyano-2-[1-(4-ethyl-3-iodo-phenyl)-1-methyl-ethyl]-1H-indole-3-carboxylate; Formula VII refers to tert-butyl 6-cyano-2-[1-[4-ethyl-3-(4-morpholino-1-piperidyl)phenyl]-1-methyl-ethyl]-1H-indole-3-carboxylate; and Formula VIII refers to 6-cyano-2-[1-[4-ethyl-3-(4-morpholino-1-piperidyl)phenyl]-1-methyl-ethyl]-1H-indole-3-carboxylic acid.

[3] The method according to [1] above, wherein the condensing agent is N,N'-diisopropylcarbodiimide, or diethyl chlorophosphate.

[4] The method according to [1] above, wherein the solvent is selected from tetrahydrofuran, acetone, and acetonitrile.

[5] The method according to [2] above, wherein the acid in (1) is acetyl chloride.

[6] The method according to [2] above, wherein the base in (2) is lithium hexamethyldisilazide, or sodium hexamethyldisilazide.

[7] The method according to [2] above, wherein the R^B in (2) is a tert-butyl group.

[8] The method according to [2] above, wherein the leaving group in (3) is a fluoro group or a chloro group.

[9] The method according to [2] above, wherein the base in (3) is sodium hydroxide, potassium phosphate, potassium carbonate, or cesium carbonate, and the reaction solvent is tetrahydrofuran.

[10] The method according to [2] above, wherein the reducing agent in (4) is sodium hydrosulfite.

[11] The method according to [2] above, wherein the palladium catalyst in (5) is a combination of π-allylpalladium chloride dimer and 2',6'-dimethoxy-2-(dicyclohexylphosphino)biphenyl (S-Phos), PEPPSI-IPent, or S-Phos Pd(crotyl)Cl; and the reaction in the step 3 is carried out in a mixed solvent of tetrahydrofuran and 1,3-dimethyl-2-imidazolidinone.

[12] The method according to [2] above, wherein the optionally substituted 6-membered saturated cyclic amine in (5) is represented by the following Formula:

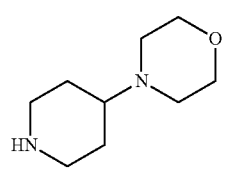

and R^{1a} is an iodo group, or a bromo group.

[13] The method according to [2] above, wherein the acid in (6) is trimethylsilyl chloride, or 2,2,2-trifluoroethanol.

[14] The method according to any one of [1] to above, wherein the Compound (1) is a hydrochloride of the Compound (1).

[15] The method according to any one of [1] to above, wherein the Compound (1) is a hydrochloride of the Compound (1), and other than the compound (1), a compound represented by Formula X is produced at 0.08% or less based on the weight of the hydrochloride of the Compound (1).

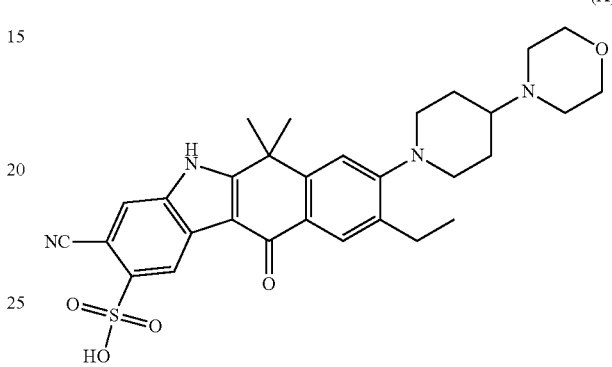

(X)

Advantageous Effects of Invention

According to the present invention, a simple and efficient, and also robust manufacturing method suitable for industrial manufacture of the Compound (1), a pharmaceutically acceptable salt thereof, or a solvate of the salt can be provided.

DESCRIPTION OF EMBODIMENTS

Figure 1:
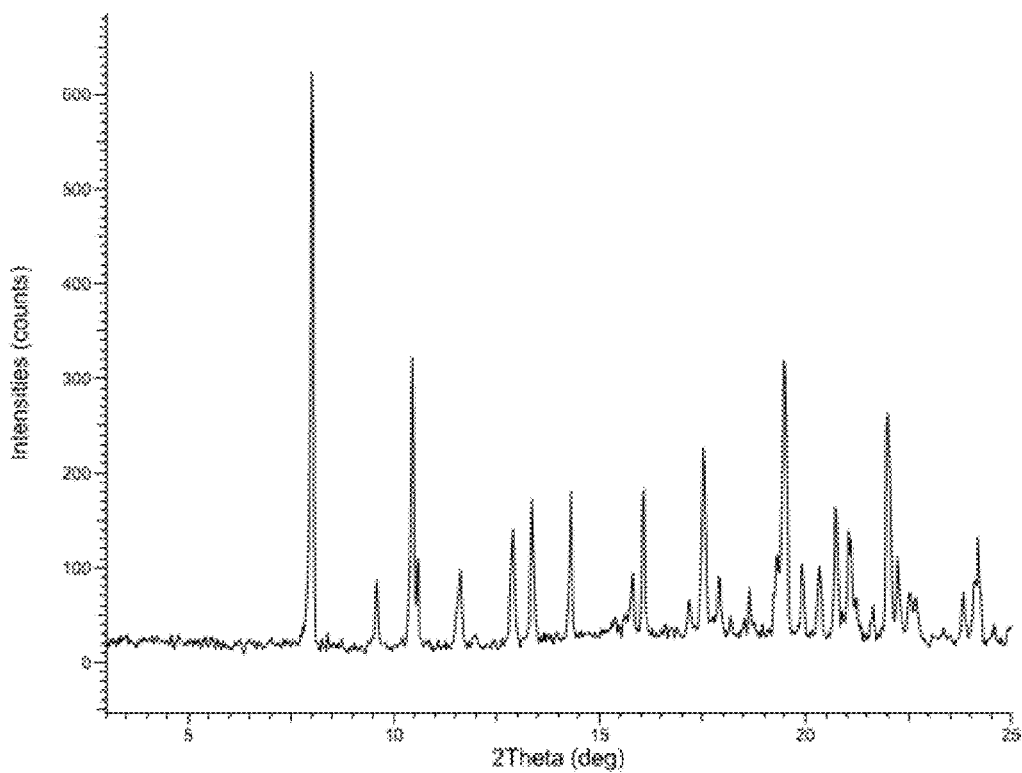
FIG. 1 is a graph of an analysis result of powder X-ray diffraction of the Compound (VIa).

The manufacturing method of the present invention will be described in detail below.

The names of reagents or solvents corresponding to the abbreviation codes or the chemical formulas generally used in the respective manufacturing steps and Examples are described below.

AcCl: acetyl chloride
AcOH: acetic acid
BINAP: 2,2'-bis(diphenylphosphino)-1,1'-binaphthyl
t-BuOK: tert-butoxypotassium
t-BuONa: tert-butoxysodium
t-Bu group: tert-butyl group
t-Butyl X-Phos: 2-di-tert-butylphosphino-2',4',6'-triisopropylbiphenyl
CDI: carbonyldiimidazole
CPME: c-pentyl methyl ether
CX-21: Allyl[1,3-bis(2,6-diisopropylphenyl)imidazol-2-ylidene]chloropalladium(II)
Dave Phos: 2-dicyclohexylphosphino-2'-(N,N-dimethylamino)biphenyl
DBU: 1,8-diazabicyclo[5.4.0]-7-undecene
DIC: N,N'-diisopropylcarbodiimide
DIPEA: N,N-diisopropylethylamine
DMA: N,N-dimethylacetamide
DME: 1,2-dimethoxyethane
DMF: N,N-dimethylformamide
DMI: 1,3-dimethyl-2-imidazolidinone
DMSO: dimethyl sulfoxide
DPPF: 1,1'-bis (diphenylphosphino)ferrocene
EtOAc: ethyl acetate
EtOH: ethanol
c-Hexyl John Phos: (2-biphenyl) dicyclohexylphosphine
John Phos: (2-biphenyl)di-tert-butylphosphine
KHMDS: potassium hexamethyldisilazide
LDA: lithium diisopropylamide
LiHMDS: lithium hexamethyldisilazide
MeCN: acetonitrile
MEK: 2-butanone
MeOH: methanol
2-MeTHF: 2-methyltetrahydrofuran
MTBE: tert-butyl methyl ether
NaHMDS: sodium hexamethyldisilazide
NMP: N-methylpyrrolidone
$Pd_2(dba)_3$: tris(dibenzylideneacetone)dipalladium(0)
PEPPSI-IPent: dichloro[1,3-bis(2,6-di-3-pentylphenyl) imidazol-2-ylidene](3-chloropyridyl)palladium(II)
S-Phos: 2',6'-dimethoxy-2-(dicyclohexylphosphino)biphenyl
S-Phos Pd(crotyl)Cl: chloro(crotyl) (2-dicyclohexylphosphino-2',6'-dimethoxybiphenyl)palladium(II)
T3P: propylphosphonic anhydride
TEA: triethylamine
TFA: trifluoroacetic acid
TFE: 2,2,2-trifluoroethanol
THF: tetrahydrofuran
TMSCl: trimethylsilyl chloride
TMSI: trimethylsilyl iodide
Xantophos: 4,5'-bis(diphenylphosphino)-9,9'-dimethylxanthene
X-Phos: 2-dicyclohexylphosphino-2',4',6'-triisopropylbiphenyl In the present invention, as a "pharmaceutically acceptable salt" of the Compound (1), for example, a hydrochloride, a hydrobromide, a hydroiodide, a phosphate, a phosphonate, a sulfate, a sulfonate such as methanesulfonate, and p-toluenesulfonate, a carboxylate, such as an acetate, a citrate, a malate, a tartrate, a succinate, and a salicylate, an alkali metal salt, such as a sodium salt, and a potassium salt, an alkaline earth metal salt, such as a magnesium salts, and a calcium salt, and an ammonium salt, such as an ammonium salt, an alkyl ammonium salt, a dialkyl ammonium salt, a trialkyl ammonium salt, and a tetraalkyl ammonium salt, are included.

A solvate of the Compound (1) or a solvate of a salt of the Compound (1) may be either a hydrate or a non-hydrate, and examples of a non-hydrate include solvates of an alcohol (such as methanol, ethanol, and n-propanol), or dimethylformamide.

A "$C_1$-$C_6$ alkyl group" is a monovalent group derived from a straight-chain or a branched-chain aliphatic hydrocarbon having 1 to 6 carbon atoms by removing an optional hydrogen atom therefrom. Specific examples thereof include a methyl group, an ethyl group, an isopropyl group, a butyl group, a n-butyl group, an isobutyl group, a sec-butyl group, a tert-butyl group, a pentyl group, an isopentyl group, and a hexyl group. A $C_1$-$C_4$ alkyl group is preferable.

As a "condensing agent" to be used in the present invention, a condensing agent used for peptide synthesis, or a mixed acid anhydridizing agent can be used. Examples of the condensing agent used for peptide synthesis include carbonyldiimidazole (CDI), N,N'-diisopropylcarbodiimide (DIC), and propylphosphonic anhydride (T3P). Examples of the mixed acid anhydridizing agent include a dialkyl chlorophosphate such as diethyl chlorophosphate. The condensing agent is preferably DIC, or diethyl chlorophosphate.

A "leaving group" refers to a group which is removed in a substitution reaction and replaced with another functional group, and examples thereof include a halogen group, such as a fluoro group, a chloro group, a bromo group, and an iodo group, a triflate group, a mesyl group, and a tosyl group. Preferably, it is a fluoro group, a chloro group, a bromo group, or an iodo group.

Specific examples of a "6-membered saturated cyclic amino group" include a 6-membered saturated cyclic group linking via a nitrogen atom, such as a piperidyl group, a piperazinyl group, a morpholino group, and a thiomorpholino group. Preferably, it is a piperidyl group.

Examples of a substituent of the "6-membered saturated cyclic amino group" include a 4 to 10-membered heterocycloalkyl group. A 4 to 10-membered heterocycloalkyl group means a 4 to 10-membered saturated ring having 1 to 3 atoms of nitrogen, oxygen, or sulfur as hetero atoms, and means a monovalent group, such as a pyrrolidinyl group, an imidazolidinyl group, a tetrahydrofuranyl group, a piperidyl group, a piperazinyl group, a morpholino group, and a thiomorpholino group. Preferably, it is a morpholino group. Further, a 4 to 10-membered heterocycloalkyl group may further have one or more substituents, and examples of the substituents include a halogen atom, a $C_1$-$C_6$ alkyl group, an oxo group, a hydroxyl group, and deuterium. A substituent of a "6-membered saturated cyclic amino group" may be a ketal group, an acyclic ketal group such as a dimethyl ketal group, or a cyclic ketal group, such as a 1,3-dioxolanyl group, and a 1,3-dioxanyl group.

Specific examples of the "6-membered saturated cyclic amine" include a 6-membered saturated cyclic amine linking via a nitrogen atom, such as piperidine, piperazine, morpholine, and thiomorpholine. Preferably, it is piperidine.

Examples of a substituent of the "6-membered saturated cyclic amine group" include a 4 to 10-membered heterocycloalkyl group. A 4 to 10-membered heterocycloalkyl group means a 4 to 10-membered saturated ring having 1 to 3 atoms of nitrogen, oxygen, or sulfur as hetero atoms, and means a monovalent group, such as a pyrrolidinyl group, an imidazolidinyl group, a tetrahydrofuranyl group, a piperidyl group, a piperazinyl group, a morpholino group, and a thiomorpholino group. Preferably, it is a morpholino group. Further, a 4 to 10-membered heterocycloalkyl group may further have one or more substituents, and examples of the substituents include a halogen atom, a $C_1$-$C_6$ alkyl group, an oxo group, a hydroxyl group, and deuterium. A substituent of a "6-membered saturated cyclic amine group" may be a ketal group, an acyclic ketal group such as a dimethyl ketal group, or a cyclic ketal group, such as a 1,3-dioxolanyl group, and a 1,3-dioxanyl group.

Examples of the "acid" include acetyl chloride, formic acid, acetic acid, methanesulfonic acid, p-toluenesulfonic acid, benzenesulfonic acid, TFA, hydrochloric acid, sulfuric acid, pyridinium p-toluenesulfonate, and TMSCl. Preferably, it is acetyl chloride, or TMSCl.

As the "base", sodium hydroxide, potassium hydroxide, lithium hydroxide, sodium phosphate, potassium phosphate, sodium carbonate, potassium carbonate, cesium carbonate, sodium hydride, LiHMDS, NaHMDS, LDA, lithium dicyclohexylamide, lithium 2,2,6,6-tetramethylpyrrolidide, KHMDS, t-BuOK, t-BuONa, or the like may be used, and a strong base reagent, such as LiHMDS, NaHMDS, t-BuOK, and DBU, or an inorganic salt reagent, such as sodium hydroxide, potassium phosphate, potassium carbonate, and cesium carbonate, is preferable.

As the "reducing agent", iron, zinc, titanium(III) chloride, tin(II) chloride, or sodium hydrosulfite may be used, and sodium hydrosulfite is preferable.

As the "palladium catalyst", a combination of a ligand and a palladium source selected from palladium acetate, $Pd_2(dba)_3$, π-allylpalladium chloride dimer, $PdCl_2(CH_3CN)_2$, $PdCl_2(PPh_3)_2$, trialkylproazaphosphatrane, $[P(t-Bu)_3PdBr]_2$, $PPh_3$, $P(o-tol)_3$, BINAP, DPPF, $P(t-Bu)_3$, Dave Phos, John Phos, c-Hexyl John Phos, S-Phos, X-Phos, t-Butyl X-Phos, PEPPSI-IPent, Xantphos, 4,5-bis[bis(3,5-bistrifluoromethylphenyl)phosphanyl]-9,9-dimethyl-9H-xanthene, 1,3-diallyldihydroimidazolium salt, S-Phos Pd(crotyl)Cl, etc., or a commercially available palladium-ligand complex, which is preferable because it is easily procurable and uniform in quality. Further preferable is π-allylpalladium chloride dimer and S-Phos, PEPPSI-IPent, or S-Phos Pd(crotyl)Cl.

An aspect of the present invention is an industrial method for manufacturing Compound (1), by which use of a substance of very high concern can be avoided, as well as the reaction selectivity can be enhanced, and formation of by-products (impurities) can be suppressed.

Scheme 1

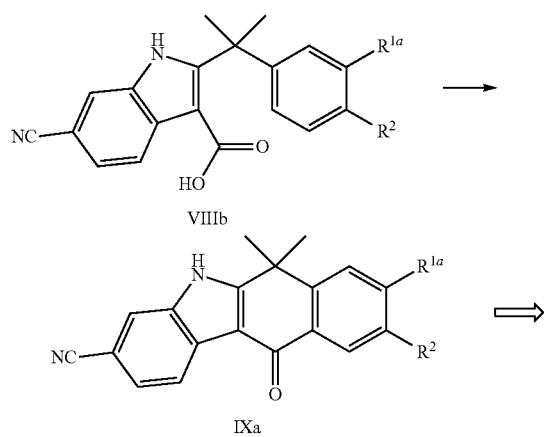

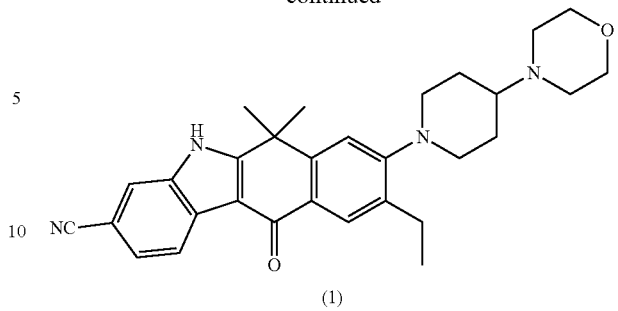

wherein $R^{1a}$ represents an optionally substituted 6-membered saturated cyclic amino group; and $R^2$ represents a $C_1$-$C_6$ alkyl group.

The present invention is a method including a cyclization step of the Compound (VIIIb) to the Compound (IXa) by a Friedel-Crafts type reaction.

The above reaction can be carried out by treating a carboxyl group in the Compound (VIIIb) with a mixed acid anhydridizing agent (such as a dialkyl chlorophosphate), or a condensing agent, such as a condensing agent used in peptide synthesis (e.g., CDI, DIC, and T3P), to convert it to a corresponding mixed anhydride or activated ester for activating the carboxyl group. The mixed acid anhydridizing agent may be used at 1 equivalent to 10 equivalents based on the substrate, and preferably at 1 equivalent to 5 equivalents. The condensing agent may be used at 1 equivalent to 10 equivalents based on the substrate, and preferably at 1 equivalent to 5 equivalents. A preferable mixed acid anhydridizing agent or condensing agent is diethyl chlorophosphate or DIC, which may be used at 1 equivalent to 5 equivalents based on the substrate. An organic base such as TEA, DIPEA, or pyridine may be also used, and DIPEA is preferable. The organic base may be used at 1 equivalent to 10 equivalents based on the Compound (VIIIb), which is a substrate, and preferably at 1 equivalent to 8 equivalents. This reaction can be carried out without a solvent, or in a solvent. In this case, examples of a solvent to be used include toluene, xylene, diethyl ether, THF, CPME, 2-methyltetrahydrofuran, MTBE, DMSO, sulfolane, 1,4-dioxane, acetone, acetonitrile, dichloromethane, 2-butanone, ethyl acetate, and isopropyl acetate, as well as a mixture thereof, which are solvents not falling within substances of very high concern. Preferable are THF, acetone, acetonitrile, and a mixture thereof. The reaction may be performed in the reaction temperature range of 0° C. to near the boiling point of the solvent, and preferably 40° C. to near the boiling point of the solvent. The reaction may be carried out by stirring a reaction mixture for a certain time period (for example, 0.1 hours to 24 hours, and preferably 1 hour to 6 hours).

After the activation reaction of a carboxylic acid represented by Formula (VIIIb), by conducting cyclization using an acid such as polyphosphoric acid under conditions described in the method of Mouaddib, et al. (Heterocycles, 1999, 51, 2127), or the like, for example, in a solvent at a reaction temperature of 0° C. to near the boiling point of the solvent, or cyclization by heating in a solvent without an additional reagent to 25° C. to near the boiling point of the solvent, a Compound (IXa) can be obtained. This reaction can be carried out by stirring a reaction mixture in the temperature range of 0° C. to near the boiling point of the solvent for a certain time period (for example, 0.1 hours to 24 hours).

Furthermore, when $R^{1a}$ is a 4-oxo-1-piperidyl group, the Compound (1) can be produced by subjecting morpholine to a reductive amination reaction condition in the presence of a reducing agent according to the method of Borch, et al. (J. Am. Chem. Soc., 1971, 93, 2897).

In this regard, a pharmaceutically acceptable salt of the Compound (1) can be produced by bringing a free form of the Compound (1) in contact with an acid or a base, which can be used for manufacturing a drug corresponding to the pharmaceutically acceptable salt.

A solvate of the Compound (1), or a solvate of a pharmaceutically acceptable salt of the Compound (1) can be produced by crystallization using a desired solvent.

Further, another aspect of this invention is related to an industrial method for manufacturing the Compound (1) including a series of steps, wherein the method does not require much effort for controlling a residual solvent, and can produce the Compound (1) and a synthetic intermediate therefor in higher yields.

An outline of a series of procedures from Compound (I) to Compound (IX) is shown in scheme 2, and each step is described below. Note that these are mere examples, and the present invention may use a part of steps 1 to 5, and use publicly known methods for other steps, and not only the specified reagents and conditions are adopted, but also another reagent or condition may be adopted to the extent the object of the present invention can be achieved. Moreover, as a raw material to be used for synthesis of the Compound (1) or its synthetic intermediate, a material on the market may be used, or it may be prepared by a conventional method as needed. As a reagent to be used for the manufacturing, a reagent on the market may be used, or it may be prepared before use by a conventional method. As a solvent to be used for the manufacturing, especially when a compound unstable to water, oxygen or carbon dioxide is handled, a dehydrated solvent or a degassed solvent on the market may be used, or a solvent which has undergone a dehydration and degassing treatment by a conventional method according to need may be used. If necessary, multiple solvents may be mixed and used as the solvent. In manufacturing the compound, when a compound unstable to water, oxygen or carbon dioxide is handled, an intended chemical reaction may be progressed efficiently by carrying out the manufacturing in a reaction system in an inert atmosphere, more specifically in a reaction system purged with a well-dried inert gas. Examples of a preferable inert gas include nitrogen, and argon. The manufacturing method of the present invention may be carried out by changing the temperature of the reaction system according to the nature and reactivity of the compound. The optimum temperature for the reaction is within the range of −100° C. with cooling with liquid nitrogen to near the boiling point of the solvent.

Scheme 2

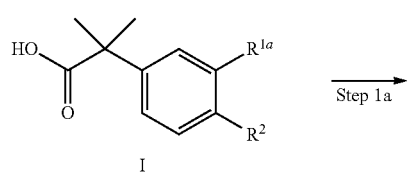

I

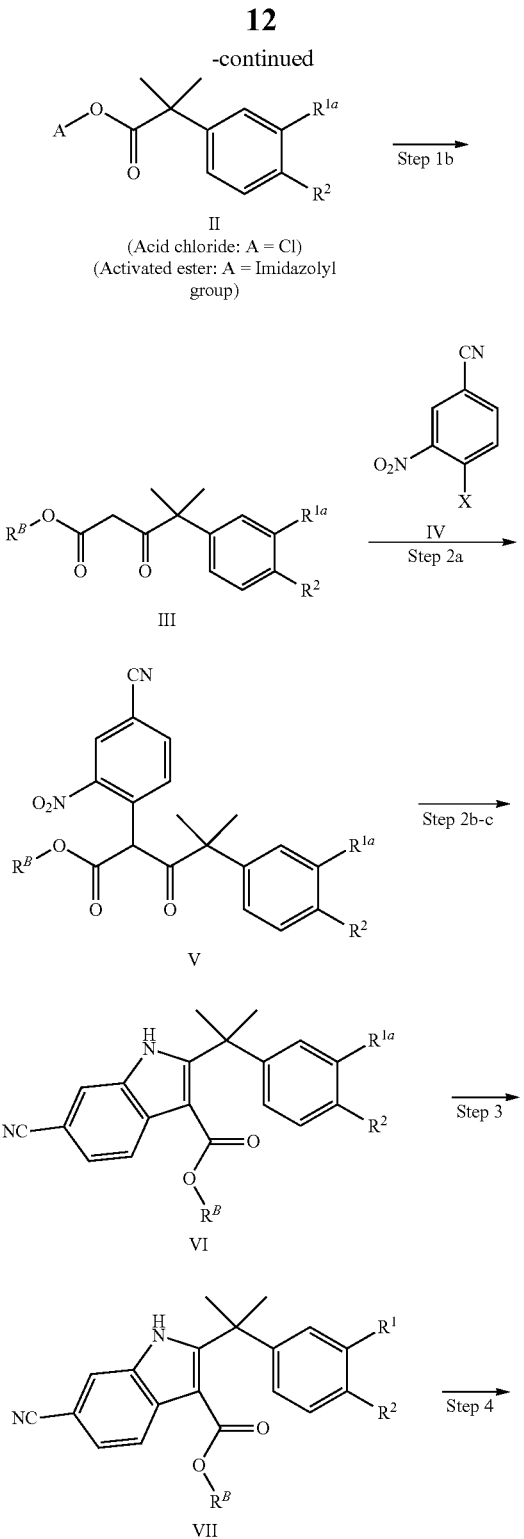

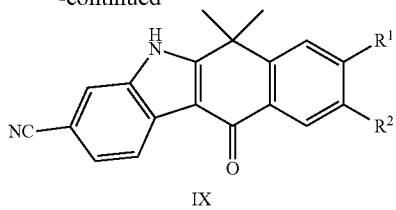

IX wherein X represents a leaving group; $R^{1a}$ represents a leaving group, or an optionally substituted 6-membered saturated cyclic amino group; 1e represents an optionally substituted 6-membered saturated cyclic amino group; $R^2$ represents a $C_1$-$C_6$ alkyl group; and $R^B$ represents a $C_1$-$C_6$ alkyl group.

Steps 1a and 1b

The steps are a process step of conversion of a carboxylic acid (I) to a β-ketoester (III). In the steps, the carboxylic acid (I) which is a starting compound can be converted to an activated carboxylic acid (II), such as an acid chloride, an activated ester, and an alkyl ester, in a solvent in the reaction temperature range of 0° C. to near the boiling point of the solvent in the presence of an activating agent. Then the activated carboxylic acid (II) is condensed with an enolate of AcOR$^B$ in the reaction temperature range of −20° C. to near the solvent boiling point to yield the β-ketoester (III).

As a conversion reaction (Step 1a) from the carboxylic acid (I) to the acid chloride (II, A=Cl), a method of converting a carboxylic acid (I) to the corresponding acid chloride (II, A=Cl) using thionyl chloride, oxalyl chloride, phosphorus oxychloride, or the like as an activating agent can be used. In this case, the usable amount of an activating agent may be 1 equivalent to 10 equivalents based on the substrate. As the solvent used for the reaction, toluene, xylene, THF, CPME, MTBE, DMSO, sulfolane, 1,4-dioxane, or the like, or a mixture thereof may be used. This reaction may be carried out in the reaction temperature range of −20° C. to near the boiling point of the solvent, and may be carried out by stirring a reaction mixture for a certain time period (for example, 0.1 hours to 24 hours).

Further, for the conversion reaction (Step 1a) from the carboxylic acid (I) to the activated ester (II, A=imidazolyl group), a method of converting the carboxylic acid (I) to the corresponding activated ester (II, A=imidazolyl group) using CDI, or the like as an activating agent may be applied. In this case, the usable amount of an activating agent may be 1 equivalent to 10 equivalents based on the substrate. Examples of the solvent usable for the reaction include toluene, xylene, THF, CPME, MTBE, DMSO, sulfolane, and 1,4-dioxane, as well as a mixture thereof. This reaction may be carried out in the reaction temperature range of −20° C. to near the boiling point of the solvent, and may be carried out by stirring a reaction mixture for a certain time period (for example, 0.1 hours to 24 hours). For producing an activated ester, a condensing agent may be used in addition to CDI, and the obtained activated ester corresponding to the condensing agent may be similarly used for manufacture of a β-ketoester (III).

In addition, for the conversion reaction (Step 1a) of a carboxylic acid (I) to an alkyl ester (II, A=OR$^A$; RA represents a $C_1$-$C_6$ straight-chain or branched-chain alkyl group), a method of converting a carboxylic acid (I) to the corresponding alkyl ester (II, A=OR$^A$) using a hydrogen chloride gas, or a combination of acetyl chloride and an alcohol (R$^A$OH) may be used. The amount of the hydrogen chloride gas, or acetyl chloride used in the reaction may be 0.1 equivalents to 10 equivalents, and preferably 2 equivalents to 5 equivalents based on the substrate. As the solvent to be used in the reaction, an alcohol (R$^A$OH) may be used. This reaction may be carried out in the reaction temperature range of −20° C. to near the boiling point of the solvent and preferably 0° C. to 50° C. This reaction may be carried out by stirring a reaction mixture for a certain time period (for example, 0.1 hours to 24 hours, and preferably 1 hour to 4 hours).

The conversion reaction of a carboxylic acid (I) to an activated carboxylic acid (II) is preferably a method using an acid chloride (II, A=Cl) obtained with thionyl chloride, a method using an activated ester obtained with CDI (II, A=imidazolyl group), or a method using an alkyl ester (II, A=OR$^A$) obtained with a combination of acetyl chloride and an alcohol.

The activated carboxylic acid (II) may be subjected to isolation and purification, or may be used successively in the next reaction without isolation and purification.

The amount of an enolate of AcOR$^B$ (R$^B$ represents a $C_1$-$C_6$ straight-chain or branched-chain alkyl group) used in the conversion reaction (Step 1b) of an activated carboxylic acid (II) to a β-ketoester (III) may be 1 equivalent to 5 equivalents, and preferably 1 equivalent to 2 equivalents based on the activated carboxylic acid (II) which is a substrate. In a method for forming an enolate of AcOR$^B$, a strong base reagent, such as LiHMDS, NaHMDS, t-BuOK, and DBU, may be used. The strong base reagent may be used in an amount of 2 equivalents to 5 equivalents, and preferably 2 equivalents to 4 equivalents based on the activated carboxylic acid (II) which is a substrate. Examples of the solvent used in the reaction may include toluene, xylene, THF, CPME, MTBE, DMSO, sulfolane, and 1,4-dioxane, as well as a mixture thereof, and THF is preferable. The AcOR$^B$ is preferably tert-butyl acetate. This reaction can be carried out in the range of −40° C. to near the boiling point of the solvent, and preferably in the range of −10° C. to 25° C. This reaction can be carried out by stirring a reaction mixture for a certain time period, for example, 0.1 hours to 24 hours, and preferably 0.1 hours to 2 hours.

Step 2a

This step is a process where a β-ketoester (III) is converted to a compound represented by Formula V by a nucleophilic aromatic substitution reaction in which an aromatic nitro compound (IV) having a leaving group (X) reacts on the ketoester in the presence of a base in the reaction temperature range of −10° C. to near the boiling point of the solvent (for example, Journal of Heterocyclic Chemistry, 2009, 46 (2), 172-177, or Organic Process Research & Development, 2014, 18 (1), 89-102).

Examples of a base to be used for the reaction include sodium hydroxide, potassium hydroxide, lithium hydroxide, sodium phosphate, potassium phosphate, sodium carbonate, potassium carbonate, cesium carbonate, sodium hydride, LiHMDS, NaHMDS, LDA, lithium dicyclohexylamide, lithium 2,2,6,6-tetramethylpyrrolidide, KHMDS, t-BuOK, and t-BuONa, and preferable are sodium hydroxide, t-BuOK, t-BuONa, potassium phosphate, sodium phosphate, potassium carbonate, or cesium carbonate. The base may be a solution dissolved in a suitable solvent. The base may be used in an amount of 1 equivalent to 10 equivalents based on the β-ketoester (III) which is a substrate, and preferably 2 equivalents to 7 equivalents.

Examples of a solvent to be used for the reaction include toluene, xylene, MeCN, THF, 2-methyltetrahydrofuran, CPME, MTBE, DMSO, sulfolane, 1,4-dioxane, acetone, 2-butanone, and water, as well as a combination thereof. Preferable are THF, water, and a combination thereof. This reaction can be carried out in the reaction temperature range of −10° C. to near the boiling point of the solvent, and preferably 0° C. to 25° C. This reaction can be carried out by stirring a reaction mixture for a certain time period (for example, 0.1 hours to 24 hours, and preferably 2 hours to 8 hours). As the leaving group (X) of the aromatic nitro compound (IV), a halogen group, such as a fluoro group, a chloro group, a bromo group, and an iodo group, a triflate group, a mesyl group, or a tosyl group may be used. Preferable is a fluoro group, or a chloro group. The aromatic nitro compound (IV) may be used in an amount of 1 equivalent to 3 equivalents based on the β-ketoester (III) which is a substrate.

In this regard, when the reaction is carried out in combination with a solvent in which the compound is not dissolved, a phase transfer catalyst can also be used, and tetramethyl ammonium chloride, tetramethyl ammonium bromide, tetramethyl ammonium hydroxide, tetraethyl ammonium chloride, tetraethylammonium bromide, tetraethylammonium hydroxide, tetrabutylammonium chloride, tetrabutylammonium bromide, tetrabutylammonium hydroxide, or the like may be used. The phase transfer catalyst may be used in an amount of 0.01 equivalents to 0.99 equivalents based on a substrate, and preferably 0.1 equivalents to 0.4 equivalents.

Step 2b-c

This step is a reductive cyclization process step in which reduction of the nitro group and then formation of an indole ring are performed. The reaction is exercisable by reducing the nitro group by making a reducing agent react on the compound represented by Formula V in the temperature range of 0° C. to near the boiling point of the solvent. Examples of the reducing agent to be used for the reaction include iron (Synthesis, 2008, (18), 2943-2952), zinc (Tetrahedron, 2008, 64 (40), 9607-9618), titanium(III) chloride (Organic & Biomolecular Chemistry, 2005, 3 (2), 213-215), tin(II) chloride (Journal of Organic Chemistry, 1993, 58 (19), 5209-5220), and sodium hydrosulfite, (Gazzetta Chimica Italiana, 1991, 121, (11), 499-504), and the most preferable reducing agent is sodium hydrosulfite. The reducing agent may be used in an amount of 1 equivalent to 20 equivalents, and preferably 2 equivalents to 6 equivalents based on the compound represented by Formula V which is a substrate. The solvent used for this reaction may be a short-chain alkyl alcohol, such as methanol, and ethanol, THF, water, or the like, as well as a combination thereof. In this case the mixing ratio of the organic solvent to water is 1/5 to 1/0.2. The reaction may be carried out in the temperature range of ° C. to near the boiling point of the solvent, and preferably 10° C. to 35° C. This reaction can be carried out by stirring a reaction mixture for a certain time period (for example, 0.1 hours to 24 hours, and preferably 1 hour to 5 hours).

Further, conditions used for reduction of a nitro group by a catalytic reduction reaction, or the like can be used (Synlett, 2008, (17), 2689-2691).

Step 3

This step relates to an aryl-nitrogen atom bonding reaction using a compound represented by Formula VI having a leaving group ($R^{1a}$), and can be carried out, for example, according to the method of Buchwald, et al. (Organic synthesis, 78, 23; Coll. Vol. 10: 423). This reaction can be carried out in a suitable solvent which is inert to the compound represented by Formula VI or reagents, in the presence of an optionally substituted 6-membered saturated cyclic amine corresponding to $R^1$ and a base in the reaction temperature range of 0° C. to near the boiling point of the solvent, and preferably 5° C. to 55° C. In this regard, the reaction for converting the leaving group ($R^{1a}$) to $R^1$ may be performed in addition to at step 3, also at step 1, step 2, step 4, or step 5, or at the final stage where the compound (IXa) having the leaving group ($R^{1a}$) is converted to the Compound (1) to the extent the reaction is not adversely affected. As the leaving group ($R^{1a}$) in the compound represented by Formula VI, a halogen group, a triflate group, or the like may be used, and preferable is a bromo group, or an iodine group. As the base to be used for the reaction, for example, t-BuONa, t-BuOK, LiHMDS, NaHMDS, KHMDS, DBU, potassium phosphate, sodium carbonate, potassium carbonate, cesium carbonate, or the like may be used. The base can be used in an amount of 1 equivalent to 5 equivalents based on the substrate. The base may be used as a solution dissolved in a suitable solvent. As the solvent to be used for the reaction may be, for example, toluene, n-hexane, EtOAc, DMI, DMSO, THF, 1,4-dioxane, or the like, as well as a mixture thereof. This step can also be carried out using a catalyst and a ligand, and as the catalyst and ligand (or a complex of a catalyst and a ligand), for example, palladium acetate, $Pd_2(dba)_3$, π-allylpalladium chloride dimer, $PdCl_2 (CH_3CN)_2$, $PdCl_2(PPh_3)_2$, trialkylproazaphosphatrane, [P(t-Bu)$_3$PdBr]$_2$, PPh$_3$, P(o-tol)$_3$, BINAP, DPPF, P(t-Bu)$_3$, Dave Phos, John Phos, c-Hexyl John Phos, S-Phos, X-Phos, t-Butyl X-Phos, Xantphos, 4,5-bis[bis(3,5-bis(trifluoromethyl)phenyl)phosphanyl]-9,9-dimethyl-9H-xanthene, or 1,3-diallyldihydroimidazolium salt may be used. The catalyst and ligand may be used in an amount of 0.001 equivalents to 0.99 equivalents based on the substrate, preferably equivalents to 0.1 equivalents, and more preferably equivalents to 0.05 equivalents. The leaving group ($R^{1a}$) is preferably a halogen group, and more preferably a bromo group, or an iodine group. An optionally substituted 6-membered saturated cyclic amine to be used in this reaction is preferably a 4-(4-piperidyl) morpholine, piperidin-4-one, or a ketal form of piperidin-4-one. The optionally substituted 6-membered saturated cyclic amine may be used in an amount of 1 equivalent to 5 equivalents, and more preferably 1 equivalent to 3 equivalents based on the substrate. The reaction may be carried out in the temperature range of ° C. to near the boiling point of the solvent, and preferably 5° C. to 40° C. This reaction can be carried out by stirring a reaction mixture in the aforedescribed temperature range for a certain time period (for example, hours to 24 hours, and preferably 0.5 hours to 2 hours).

In this step, it is preferable to form a salt of the compound represented by Formula VII. The salt of the compound represented by Formula VII can be produced by bringing an acid or a base usable for manufacturing a drug corresponding to a predetermined salt, preferably a pharmaceutically acceptable salt, with a free form of the compound represented by Formula VII. A hydrochloride of the compound represented by Formula VII is preferable.

Step 4

This step relates to a reaction for converting the compound represented by Formula VII to a compound represented by Formula VIII through a deprotection step for the ester protecting group ($R^B$) wherein $R^B$ are as defined above. As the ester protecting group ($R^B$), for example, a $C_1$-$C_6$ alkyl group can be used, however, a tert-butyl group is preferable. The deprotection may be carried out, for example, by the methods described in "Greene, and Wuts, 'Protective Groups in Organic Synthesis', (5th Edition, John Wiley & Sons, 2014)", and these may be used appropriately corresponding to reaction conditions. When the ester protecting group ($R^B$) is a tert-butyl group, as the deprotection reagent, for example, TMSI, TMSCl, or $BF_3 \cdot OEt_2$ can be used. The deprotection reagent may be used in an amount of 1 equivalent to 10 equivalents based on the substrate, and preferably 1.5 equivalents to 3 equivalents. Examples of the solvent to be used for the reaction may include toluene, xylene, diethyl ether, THF, CPME, MTBE, DMSO, sulfolane, 1,4-dioxane, 2,2,2-trifluoroethanol, and a mixture thereof, and preferable is THF, 2,2,2-trifluoroethanol, or a mixture thereof. The reaction may be carried out in the temperature range of −20° C. to near the boiling point of the solvent, and preferably 0° C. to 35° C. This reaction can be carried out in the aforedescribed temperature range by stirring a reaction mixture for a certain time period (for example, 0.1 hours to 24 hours, and preferably 1 hour to 8 hours).

Step 5 is a step in the Scheme 1 described above.

The hydrochloride of the Compound (1) can be produced by bringing the Compound (1) in contact with hydrogen chloride. The Compound (1) is dissolved in a suitable solvent, and hydrogen chloride is added thereto to prepare a solution of a hydrochloride of the Compound (1). Then, if necessary, a poor solvent is added to the solution to crystallize a hydrochloride of the Compound (1), thereby producing the hydrochloride of the Compound (1). Further, by mixing a solution of the Compound (1) and hydrogen chloride to precipitate a hydrochloride of the Compound (1), a hydrochloride of the Compound (1) can be produced.

As a solvent suitable for dissolving the Compound (1), acetone, 2-butanone, tetrahydrofuran, dimethylformamide, dimethylacetamide, N-methylpyrrolidone, dimethylsulfoxide, acetic acid, water, or a mixed solvent of those selected from the above may be used. Preferable is a mixed solvent of 2-butanone, acetic acid, and water.

Examples of a method of adding hydrogen chloride include a method of adding a hydrogen chloride gas, and a method of adding a hydrochloric acid solution having dissolved hydrogen chloride. Examples of the hydrochloric acid solution having dissolved hydrogen chloride include an aqueous solution of hydrochloric acid, a methanol solution of hydrochloric acid, an ethanol solution of hydrochloric acid, an ethyl acetate solution of hydrochloric acid, and a tetrahydrofuran solution of hydrochloric acid. Preferable is an ethanol solution of hydrochloric acid.

Examples of a poor solvent to be added for crystallizing a hydrochloride of the Compound (1) include hexane, heptane, petroleum ether, ethanol, and water.

Further, a hydrochloride of the Compound (1) may be produced by adding a hydrochloric acid solution in which hydrogen chloride is dissolved into a solution having dissolved the Compound (1), or by adding a solution in which the Compound (1) is dissolved into a hydrochloric acid solution having dissolved hydrogen chloride. Furthermore, a solution having dissolved the Compound (1) can be used after removal of insolubles in the solution for manufacturing a hydrochloride of the Compound (1). Examples of the method for removing insolubles include, but not limited to, filtration and centrifugation.

The hydrochloride of the Compound (1) may be an anhydride, or in the form of a solvate such as a hydrate. In this case, "solvation" is a phenomenon in which a solute molecule or an ion strongly attracts molecules in the vicinity thereof in the solution to form a molecule cluster. For example, in a case where the solvent is water, the phenomenon is called hydration, and the substance obtained by hydration is called hydrate. The solvate may be either a hydrate or a non-hydrate. As a non-hydrate, there are solvates containing an alcohol (such as methanol, ethanol, n-propanol, and 2-propanol), tetrahydrofuran, dimethyl sulfoxide, and the like.

More specific manufacturing methods are described in Japanese Patent No. 4588121, Japanese Patent No. 4918630, and Japanese Patent Laid-Open No. 2012-126711.

The present invention can solve various problems in the conventional method.

Specifically, the manufacturing method of the present invention is particularly useful in the following respects.

(1) In the case of a reduction reaction using sodium hydrosulfite (Steps 2b-c) described as a preferable reducing agent in Patent Literature 1, Impurity (X) is simultaneously produced, which remains up to a bulk pharmaceutical, and therefore a great deal of effort is required for controlling its residual amount for securing the safety of the bulk pharmaceutical.

It is stipulated that Impurity (X) may be accepted up to 0.15% at most based on the weight of the Compound (1) (in the case of a salt or a solvate, a salt or a solvate of the Compound (1)) as impurities pharmaceutically acceptable to a compound represented by the Compound (1), a pharmaceutically acceptable salt thereof, or a solvate thereof, or a pharmaceutical composition thereof. In contrast, in the case of the manufacturing method of the present invention, its amount can be suppressed ordinarily to about 0.08% or less, specifically in the range of 0.001% to about 0.08%, preferably in the range of about 0.001% to about 0.08%, and more preferably in the range of about 0.001% to about 0.05%. Further, Impurity (X) does not affect the pharmacological properties as a pharmaceutical composition in the specified range. Also, Impurity (X) can constitute a clear hallmark (fingerprint) indicating that a Compound (1) was produced by the manufacturing method of the present invention.

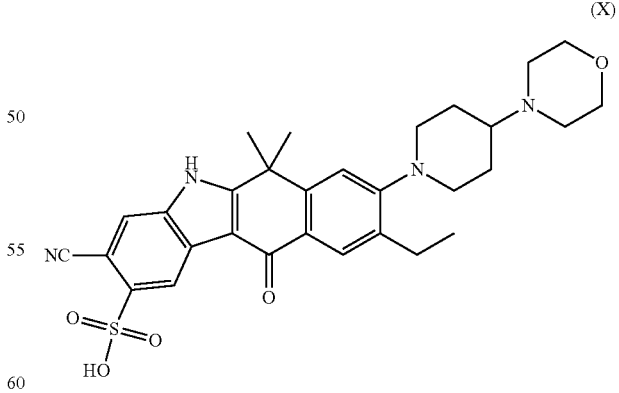

(X)

(2) In the case of the Friedel-Crafts reaction shown in step 5 of Patent Literature 1, the product yield was lowered due to Impurity (Y) by-produced in the reaction which is a regioisomer of Compound (1), which was a cause of low productivity in an industrial operation.

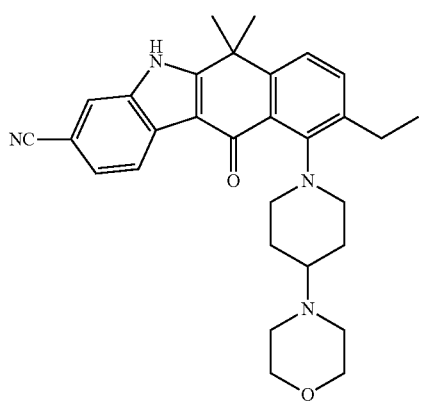
(Y)

According to the present invention, by using a condensing agent used for peptide synthesis as a reaction activator for a Friedel-Crafts reaction, formation of Impurity (Y) which was a cause of decrease in the yield, can now be reduced significantly.

(3) Amide solvents, such as DME, DMF, and DMA, described as preferable solvents in Patent Literature 1 have recently been reported to have concerns such as carcinogenicity and teratogenicity, and they have been classified as substances of very high concern (SVHC) in the REACH Regulation, which is the regulation concerning restriction of chemicals in Europe. Therefore, restriction may be imposed on their handling.

Furthermore, according to ICH Q3C (Impurities: Guideline for Residual Solvents), the acceptable amount of an amide solvent such as DME, DMF, and DMA remaining in a bulk pharmaceutical is strictly regulated. In the actual manufacturing technology, it takes a lot of effort to control the residual solvent in order to keep the amount of the residual solvent below the regulated amount.

On the other hand, the manufacturing method of the present invention is a manufacturing method which does not use a substance of very high concern (SVHC), and therefore the control of the residual solvent is easier.

(4) In the catalytic reaction (Step 3) using a Pd-carbene complex described as a preferable catalytic system in Patent Literature 1, the content of water or an alcohol in the reaction system has a strong adverse effect on the reactivity. In order to maintain the reproducibility of the reaction, a great deal of effort was required to control the water or alcohol content in the reaction system. On the other hand, the manufacturing method of the present invention uses a catalytic reaction that is less susceptible to the content of water or an alcohol in the reaction system, and exhibits a highly reproducible catalytic reaction, namely a reaction with high robustness.

EXAMPLES

The present invention will be specifically described by way of Examples below, provided that each of them is a mere example, and the present invention is not limited thereto.

The purity by HPLC was analyzed using an H-Class system, and an Alliance system manufactured by Waters Corporation, or an LC-10 system manufactured by Shimadzu Corporation. As a column, a universally used column, such as an X-Bridge (BEH 4.6 mm ID×150 mm, or BEH 4.6 mm ID×50 mm), and a SunFire (4.6 mm ID×150 mm, or 4.6 mm ID×50 mm) manufactured by Waters Corporation, was used for analysis. Although the detection of each compound was performed using a photodiode array detector, other methods, such as a mass spectrometer, and evaporative light scattering detection may be used. The residual solvent was analyzed by an internal standard method using a GC 2010 manufactured by Shimadzu Corporation. The moisture content was measured by the Karl Fischer method (electrolytic method) using a moisture measuring device (CA-200) manufactured by Mitsubishi Chemical Analytech Co., Ltd. NMR was measured using a nuclear magnetic resonance apparatus JNM-ECP-500 (manufactured by JEOL). A powder X-ray diffraction analysis was performed using an X-ray diffractometer Empyrean (manufactured by PANalytical).

The product of each step was analyzed by the following conditions and evaluated.

| Example | Column | Gradient conditions | Product detection time |
|---|---|---|---|
| Step 1 (IIIa) | BEH 50 mm | A: 10 mM Aqueous ammonium acetate solution B: 10 mM Ammonium acetate methanol solution A:B = 50:50 (0 min.) −20:80 (2 min.) −0:100 (6 min. −10 min.) | Approx. 4.8 min. |
| Step 2 (VIa) | BEH 50 mm | A: 10 mM Aqueous ammonium acetate solution B: 10 mM Ammonium acetate methanol solution A:B = 70:30 (0 min.) −10:90 (7 min.) −0:100 (10 min. −15 min.) | Approx. 8.8 min. |
| Step 3 (VIIa HCl salt) | BEH 150 mm | A: 10 mM Aqueous ammonium acetate solution B: 10 mM Ammonium acetate methanol solution A:B = 30:70 (0 min.) −0:100 (10 min. −15 min.) | Approx. 8.5 min. |
| Step 4 (VIIIa) | Sunfire 150 mm | A: 0.5% TFA solution B: 0.5% TFA Acetonitrile solution A:B = 95:5 (0 min.) −0:100 (17 min. −20 min.) | Approx. 8.7 min. |
| Step 5 (1) | Sunfire 150 mm | A: 0.5% TFA solution B: 0.5% TFA Acetonitrile solution A:B = 95:5 (0 min.) −50:50 (17 min.) −0:100 (26 min.) | Approx. 15 min. |
| Step 6 (1) | Sunfire 150 mm | A: 0.5% TFA solution B: 0.5% TFA Acetonitrile solution A:B = 95:5 (0 min.) −50:50 (17 min.) −0:100 (26 min.) | Approx. 15 min. |

Powder X-ray diffraction analysis was obtained under the following conditions.

Polar cathode: Cu, Tube voltage: 45 kV, Tube current: 40 mA

Scanning method: continuous, step size: 0.0262606°

Scanning axis: 2θ, Time per step: 5.100 seconds

Scanning range: 3 to 25°

Example 1

Method for synthesizing tert-butyl 4-(4-ethyl-3-iodo-phenyl)-4-methyl-3-oxo-pentanoate (IIIa)

(1) Synthesis of tert-butyl 4-(4-ethyl-3-iodo-phenyl)-4-methyl-3-oxo-pentanoate (IIIa) [Step 1]

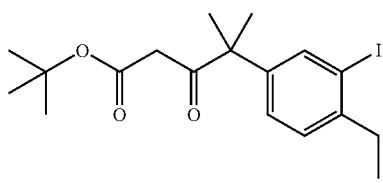

(IIIa)

In a nitrogen stream, 2-(4-ethyl-3-iodo-phenyl)-2-methyl-propanoic acid (Ia, 80 g, 251 mmol) was dissolved in methanol (240 mL). The inside temperature of the reaction mixture was lowered to −3° C., and acetyl chloride (79 g, 1.01 mol) was added to this reaction mixture, such that the reaction temperature did not exceed 20° C. After completion of the addition, the reaction mixture was heated r temperature reached 40° C. and the solution was stirred for 2 hours. The obtained solution was concentrated to 160 mL, to which MTBE (400 mL) and a saline solution (10 wt %, 320 mL) were added, and the organic layer was separated. The obtained organic layer was further washed with an aqueous solution of sodium hydrogen carbonate (5 wt %, 320 mL). The resulting organic layer was concentrated to 160 mL, to which THF (400 mL) was added, and then concentrated again to 160 mL to yield a crude product concentrate of methyl 2-(4-ethyl-3-iodo-phenyl)-2-methyl-propanoate (IIa).

THF (80 mL) was added to the obtained concentrate, and the inside temperature of the reaction mixture was lowered to −6° C. LiHMDS (THF solution, 1.3 mol/L, 464 mL) was added such that reaction temperature did not exceed 5° C., and then the reaction temperature was heated to −3° C. To this solution, tert-butyl acetate (32 g, 277 mmol) was added such that the inside temperature of the reaction mixture did not exceed 15° C., and the mixture was stirred at the same temperature for 1 hour.

To the obtained reaction mixture, a 6 mol/L hydrochloric acid (210 mL, 1.3 mol) was added such that the inside temperature of the reaction mixture did not exceed 20° C., and the solution was stirred for 30 min, and then left standing to discharge the aqueous layer. The obtained organic layer was further washed with an aqueous solution of sodium hydrogen carbonate (5 wt %, 160 mL), and concentrated to 160 mL. To the obtained concentrate, THF (400 mL) was added and concentrated to 160 mL to yield a crude product concentrate of IIIa.

The obtained concentrate was used as it was in the next step.

HPLC purity: 99.13%

(2) Synthesis of tert-butyl 6-cyano-2-[1-(4-ethyl-3-iodo-phenyl)-1-methyl-ethyl]-1H-indole-3-carboxylate (VIa) [Step 2]

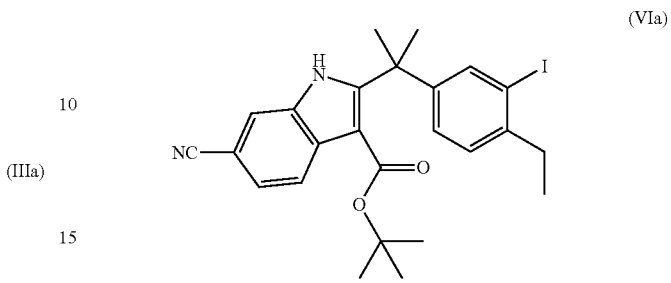

(VIa)

The THF solution (about 160 mL) of tert-butyl 4-(4-ethyl-3-iodo-phenyl)-4-methyl-3-oxo-pentanoate (IIIa) obtained in Step 1, and 4-fluoro-3-nitrobenzonitrile (IVa, 54.3 g, 327 mmol) were mixed, to which THF (742 mL) was further added, and the inside temperature of the reaction mixture was lowered to 5° C. An 8 mol/L aqueous solution of sodium hydroxide (210 mL, 1680 mmol) was added to the reaction mixture such that the inside temperature of the reaction mixture did not exceed 15° C., and the liquid was stirred at the same temperature for 4 hours. To the reaction mixture a 6 mol/L hydrochloric acid (293 mL, 1758 mmol) was added and reaction mixture the aqueous layer was discharged after raising the inside temperature of the reaction mixture to 25° C. Sodium hydrosulfite (253.9 g, 1260 mmol) was added to the obtained organic layer, and water (1000 mL) was dropped over 30 min. After completion of the dropwise addition, the reaction mixture was stirred at an inside temperature of 25° C. for 3 hours, and the aqueous layer was discharged after MTBE (314 mL) added to the reaction mixture. The obtained organic layer, to which a 1 mol/L hydrochloric acid (126 mL, 126 mmol) was added, was stirred at 25° C. for 1 hour, and a 1 mol/L aqueous solution of sodium hydroxide (293 mL, 293 mmol) was added thereto, then the aqueous layer was discharged after stirring. The resulting organic layer was washed with a 0.5 mol/L aqueous solution of sodium hydroxide (419 mL, 209.5 mmol). The washed organic layer was concentrated to about 160 mL, ethanol (314 mL) was added thereto, and it was concentrated again to 160 mL. The series of operations was repeated twice, and ethanol (1000 mL) was added to the obtained concentrated mixture, and the inside temperature of the reaction mixture was heated to 60° C. to dissolve the mixture. Water (115 mL) was added thereto over 15 min, and then the Compound VIa (524 mg) obtained by the production method described in WO 2010143664 was added as a seed crystal. Precipitation of crystals was confirmed, and the liquid was stirred at the same temperature for 1 hour. Water (230 mL) was dropped to the slurry at the same temperature over 2 hours, and then the inside temperature of the reaction mixture was lowered to 20° C. over 4 hours. The liquid was stirred for 1 hour after cooling, and a wet powder was collected by filtration. The wet powder was washed with a mixed solvent of ethanol and water (ethanol:water=10:3, total 520 mL). The wet powder was dried under a reduced pressure at the outside temperature of 50° C. to yield 95.96 g of tert-butyl 6-cyano-2-[1-(4-ethyl-3-iodo-phenyl)-1-methyl-ethyl]-1H-indole-3-carboxylate (VIa) was obtained in (yield 74.2%).

HPLC purity: 99.52%

Powder X-ray diffraction analysis: Compound (VIa) exhibited a pattern as shown in FIG. 1.

(3) Production of tert-Butyl 6-cyano-2-[1-[4-ethyl-3-(4-morpholino-1-piperidyl)phenyl]-1-methyl-ethyl]-1H-indole-3-carboxylate hydrochloride (hydrochloride of VIIa) [Step 3]

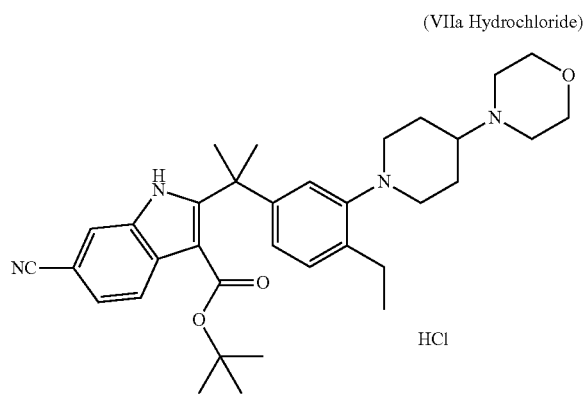 [SMILES: CCc1ccc(C(C)(C)c2[nH]c3cc(C#N)ccc3c2C(=O)OC(C)(C)C)cc1N1CCC(N2CCOCC2)CC1 ; Cl]

(VIIa Hydrochloride)

Figure 2:
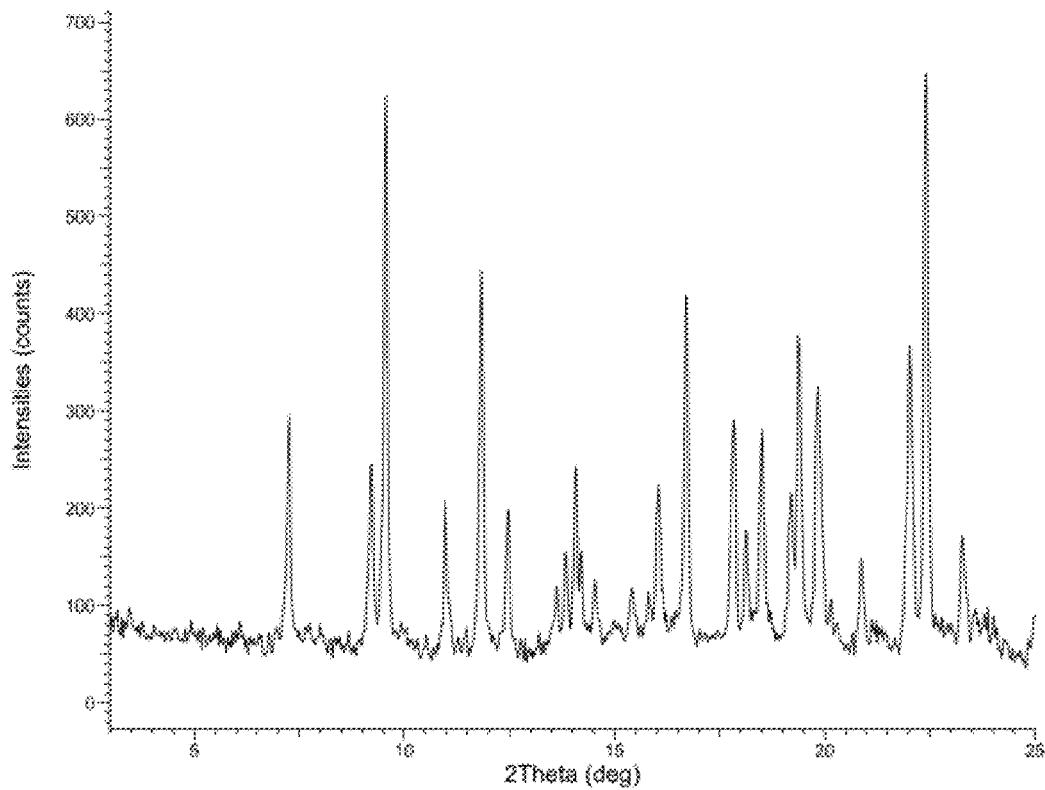
FIG. 2 is a graph of an analysis result of powder X-ray diffraction of the Compound (VIIa).
Figure 3:
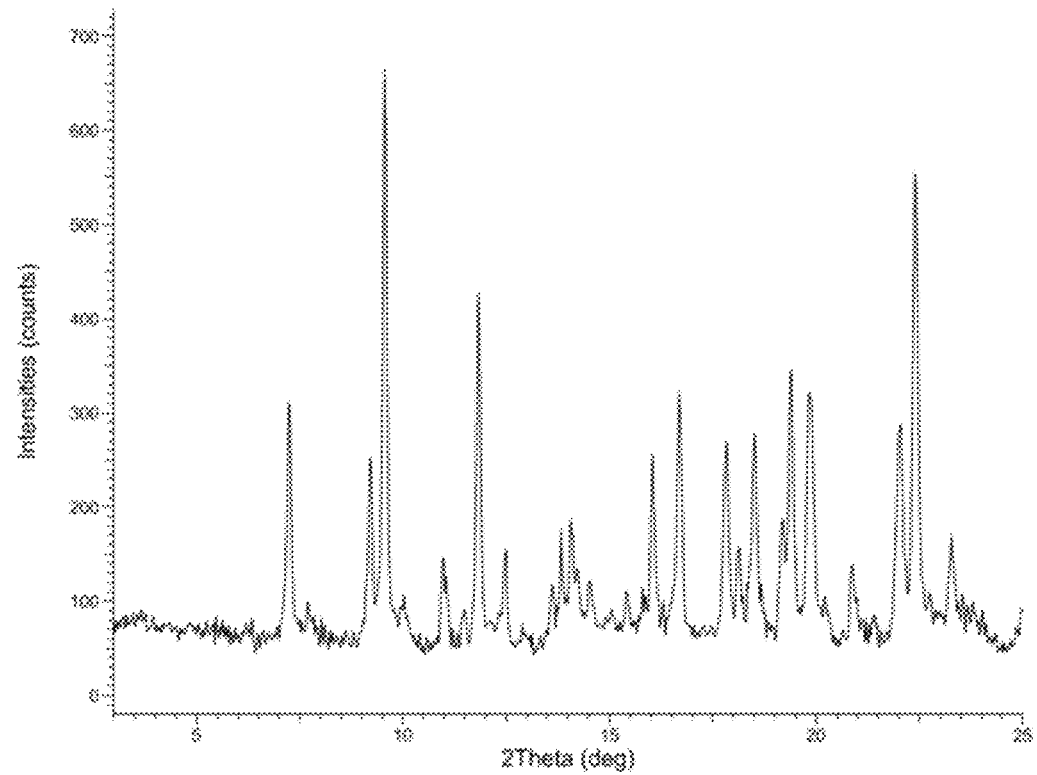
FIG. 3 is a graph of an analysis result of powder X-ray diffraction of the Compound (VIIa).
Figure 4:
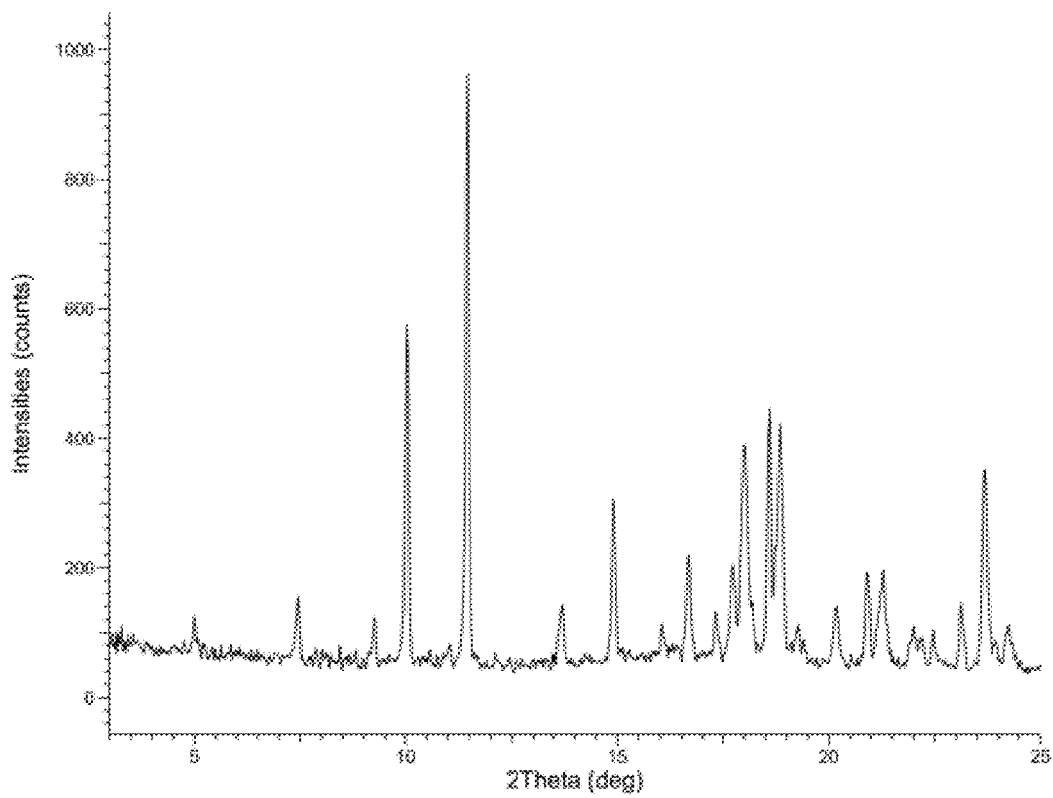
FIG. 4 is a graph of an analysis result of powder X-ray diffraction of the Compound (VIIa).

In a nitrogen atmosphere, t-allylpalladium chloride dimer (0.453 g, 2.48 mmol) and S-Phos (1.02 g, 2.48 mmol) were dissolved in THF (275 mL), and the inside of the reaction vessel was purged with nitrogen. To the obtained mixture, tert-butyl 6-cyano-2-[1-(4-ethyl-3-iodo-phenyl)-1-methyl-ethyl]-1H-indole-3-carboxylate (VIa, 85 g, 165 mmol) yielded in Step 2, 4-(4-piperidinyl)-morpholine (33.8 g, 198 mmol), and 1,3-dimethyl-2-imidazolidinone (149 mL) were added, and the inside of the reaction vessel was purged again with nitrogen. The mixture was cooled to 0° C., and NaHMDS (40% solution of THF, 280 mL, 545 mmol) was added such that the reaction temperature did not exceed 20° C. After completion of the addition, the reaction temperature was set at 25° C., and the mixture was stirred for 1 hour. Isopropyl acetate (340 mL), and an aqueous solution of ammonium chloride (15%, 255 g) were added thereto, the reaction temperature was heated to 50° C., and the liquid was stirred at the same temperature for 1 hour. the aqueous layer was discharged, and the resulting organic layer was concentrated at an outside temperature of 50° C. under a reduced pressure until the organic layer was concentrated to about 210 mL. Isopropyl acetate (340 mL) was added, then the liquid was concentrated to about 210 mL under a reduced pressure at the same temperature, and the residue was dissolved in acetone (255 mL). The solution was filtrated with a 1 μm-pore filter paper, and acetone (935 mL) was added to the obtained filtrate. After raising the temperature of the solution to 35° C., a mixed solution of an ethanol solution (21.3 mL) of pyridine hydrochloride (21 g, 182 mmol) and acetone (42.5 mL) was added dropwise over 1 hour to crystallize the objective substance. The resulting slurry was cooled to −4° C. over 1 hour, and filtrated to obtain a wet powder, which was then washed with acetone (425 mL). The wet powder was dried under a reduced pressure at an outside temperature of 40° C., to yield 97.1 g of tert-butyl 6-cyano-2-[1-[4-ethyl-3-(4-morpholino-1-piperidyl)phenyl]-1-methyl-ethyl]-1H-indole-3-carboxylate hydrochloride (hydrochloride of VIIa) (yield: 91%).
    HPLC purity: 99.13%
    Acetone content: 7.8%
    Powder X-ray diffraction analysis: Compound (VIIa) exhibited patterns as shown in FIG. 2, FIG. 3, and FIG. 4.

Example 2

Comparison in reaction selectivity and reaction rate among reagent and solvent types Using the combination of a solvent and a catalyst shown in Table 1, and carrying out the method described in Example 1, the yields of the objective substance (Compound (VIIa)) and Impurity (Z) were measured.

The comparison in the reaction selectivity and reaction rate among the reagent and solvent types is entered in Table 1.

In this regard, Impurity (Z) is a compound shown below in which the iodine group, namely a leaving group, is replaced with a hydrogen atom.

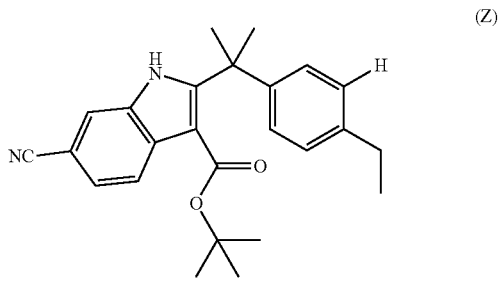 [SMILES: CCc1ccc(C(C)(C)c2[nH]c3cc(C#N)ccc3c2C(=O)OC(C)(C)C)cc1]

(Z)

TABLE 1

| Solvent | Catalyst | Selectivity (Objective substance/Impurity) | Reaction rate |
|---|---|---|---|
| DME (SVHC) | CX-21 | 28 | 100% |
| THF | PEPPSI-IPent | 37 | 100% |
| THF | S-Phos-Pd(Crotyl)Cl | 6 | 79% |
| THF/DMI | S-Phos + [Pd(allyl)Cl]$_2$ (1:1) | 30 | 100% |
| THF | Xantophos + [Pd(allyl)Cl]$_2$ | Not calculated | 39% |
| THF | PdCl$_2$(PPh$_3$)$_2$ | 0 | 65% |

From the above results, it has become clear that by using THF alone or a mixed solvent of THF and DMI, together with a predetermined catalyst, in place of DME that is a substance of very high concern, the objective substance can be obtained at a selectivity equal to or even higher than a case where DME is used.

Example 3

(1) Production of 6-cyano-2-[1-[4-ethyl-3-(4-morpholino-1-piperidyl)phenyl]-1-methyl-ethyl]-1H-indole-3-carboxylic acid (VIIIa) [Step 4]

A. Synthesis Method Using a Mixture of Acetone and Water in a Crystal Washing Method

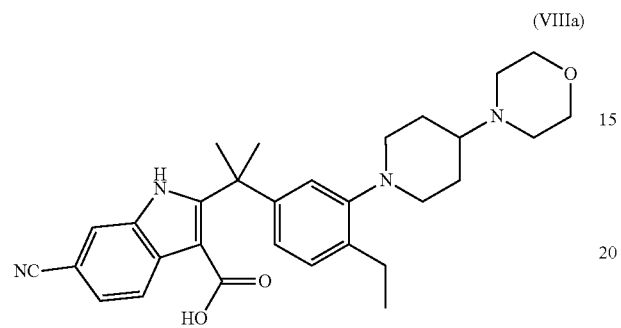
(VIIIa)

In a nitrogen atmosphere, tert-butyl 6-cyano-2-[1-[4-ethyl-3-(4-morpholino-1-piperidyl)phenyl]-1-methyl-ethyl]-1H-indole-3-carboxylate hydrochloride (VIIa, 80 g, 135 mmol) was suspended in TFE (400 mL), and the reaction mixture was stirred at an inside temperature of 25° C. Trimethylsilyl chloride (24.9 g, 229 mmol) was added such that the reaction temperature did not exceed 30° C., and the liquid was stirred at the same temperature for 2 hours. The reaction temperature was cooled to 8° C., and acetone (320 mL) was added such that the inside temperature of the reaction mixture did not exceed 12° C. To the obtained solution, a 1 mol/L aqueous solution of sodium hydroxide (241 mL) was added such that the reaction temperature did not exceed 8° C., and after crystallization, a 10% aqueous solution of dipotassium hydrogen phosphate (80 g) was added to the reaction mixture, and the mixture was stirred at the same temperature for one and a half hours. The yielded solid was filtrated and collected as a wet powder, and then the wet powder was washed with a mixed solution of acetone and water (acetone:water=1:1, total 320 mL). The wet powder was dried under a reduced pressure at an outside temperature of 50° C. to yield 6-cyano-2-[1-[4-ethyl-3-(4-morpholino-1-piperidyl)phenyl]-1-methyl-ethyl]-1H-indole-3-carboxylic acid (VIIIa, 64.138 g) (yield 91%).

HPLC purity: 99.71%
TFE content: 1.7%
Acetone content: 1.3%
Moisture content: 0.4%

B. Synthesis Method Using Water and Acetone in a Crystal Washing Method

In a nitrogen atmosphere, tert-Butyl 6-cyano-2-[1-[4-ethyl-3-(4-morpholino-1-piperidyl)phenyl]-1-methyl-ethyl]-1H-indole-3-carboxylate hydrochloride (VIIa, 20 g, 34 mmol) was suspended in TFE (100 mL), and the reaction mixture was stirred at 25° C. of reaction temperature. Trimethylsilyl chloride (6.2 g, 57 mmol) was added such that the reaction temperature did not exceed 30° C., and the mixture was stirred at the same temperature for 3 hours. The reaction temperature was lowered to 8° C., and acetone (80 mL) was added such that the reaction temperature did not exceed 12° C. To the obtained solution, a 1 mol/L aqueous solution of sodium hydroxide (61 mL) was added such that the reaction temperature did not exceed 12° C., and after crystallization, a 10% aqueous solution of dipotassium hydrogen phosphate (20 g) was added to the reaction mixture, and the liquid was stirred at the same temperature for one and a half hours. The yielded solid was filtrated and collected as a wet powder, and then the wet powder was washed with water (80 mL) and further washed with acetone (80 mL). The wet powder was dried under a reduced pressure at an outside temperature of 50° C. to yield 6-cyano-2-[1-[4-ethyl-3-(4-morpholino-1-piperidyl)phenyl]-1-methyl-ethyl]-1H-indole-3-carboxylic acid (VIIIa, 15.8 g) (yield 93%).

Figure 5:
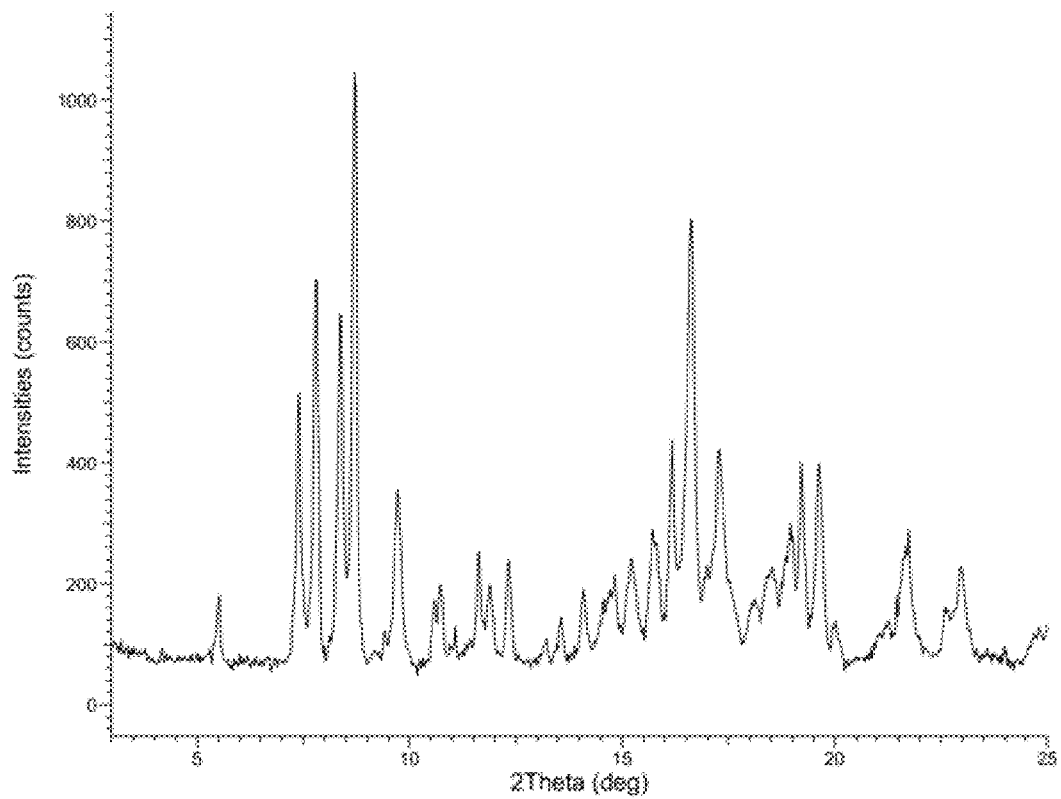
FIG. 5 is a graph of an analysis result of powder X-ray diffraction of the Compound (VIIIa).
Figure 6:
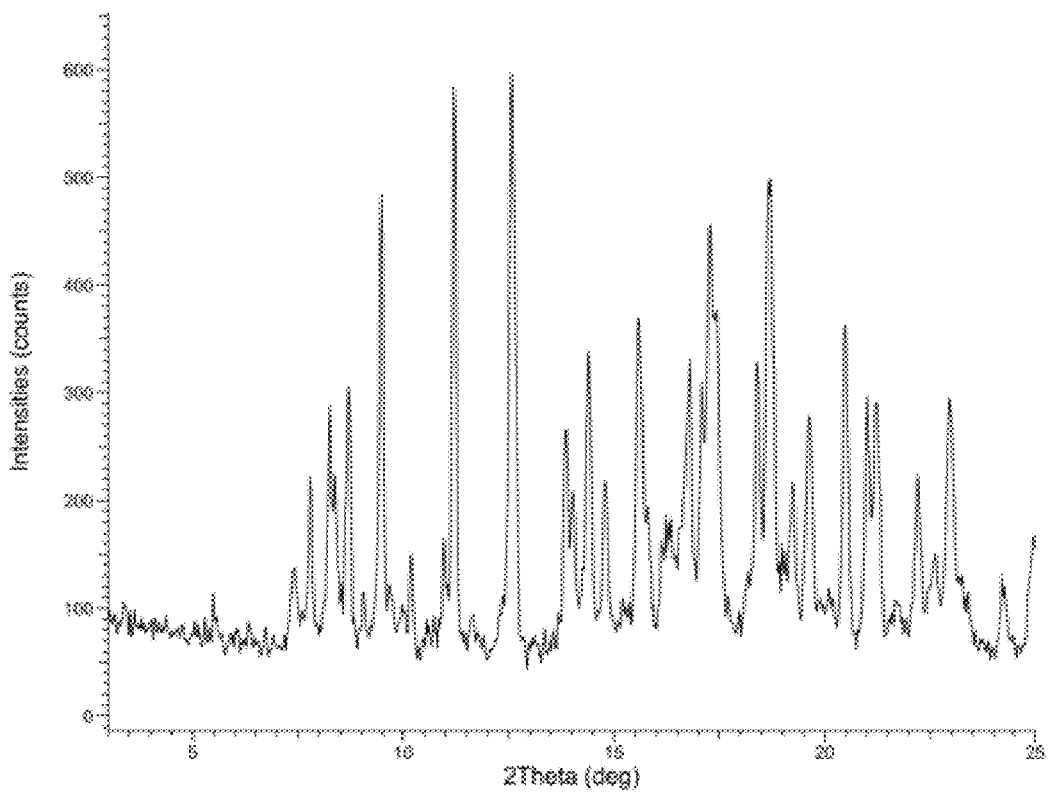
FIG. 6 is a graph of an analysis result of powder X-ray diffraction of the Compound (VIIIa).
Figure 7:
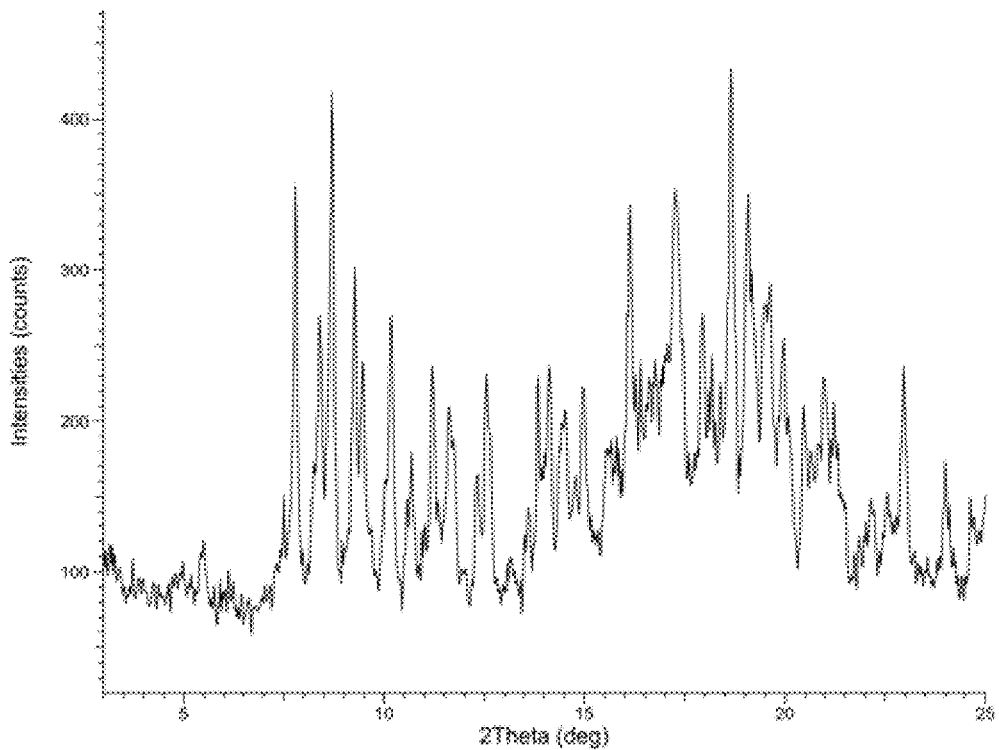
FIG. 7 is a graph of an analysis result of powder X-ray diffraction of the Compound (VIIIa).

HPLC purity: 99.76%
TFE content: 1.6%
Acetone content: 2.3%
Moisture content: 0.4%
Powder X-ray diffraction analysis: Compound (VIIIa) exhibited patterns as shown in FIG. 5, FIG. 6, and FIG. 7.

(2) Production of 9-ethyl-6,6-dimethyl-8-[4-(morpholin-4-yl)piperidin-1-yl]-11-oxo-6,11-dihydro-5H-benzo[b]carbazole-3-carbonitrile (1) [Step 5]

A. Manufacturing Method Using N,N'-Diisopropylcarbodiimide

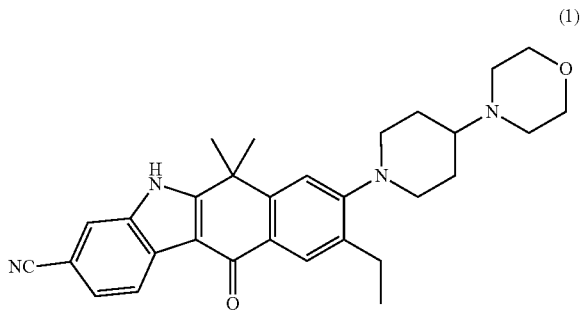 [SMILES: CCc1cc2c(cc1N1CCC(N3CCOCC3)CC1)C(C)(C)c1[nH]c3cc(C#N)ccc3c1C2=O]
(1)

Figure 8:
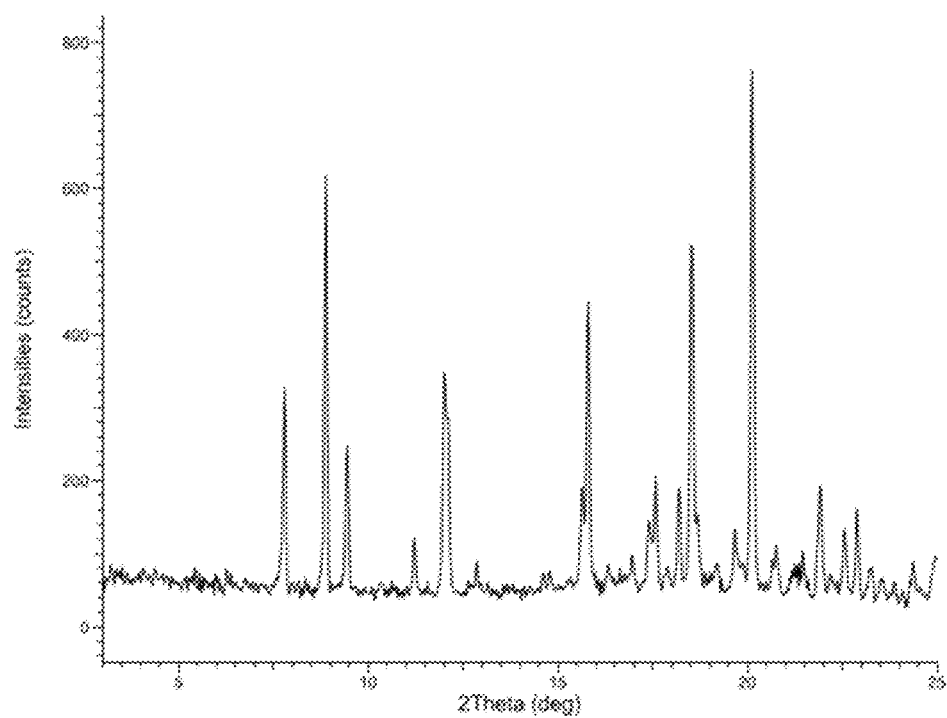
FIG. 8 is a graph of an analysis result of powder X-ray diffraction of the Compound (1).
Figure 9:
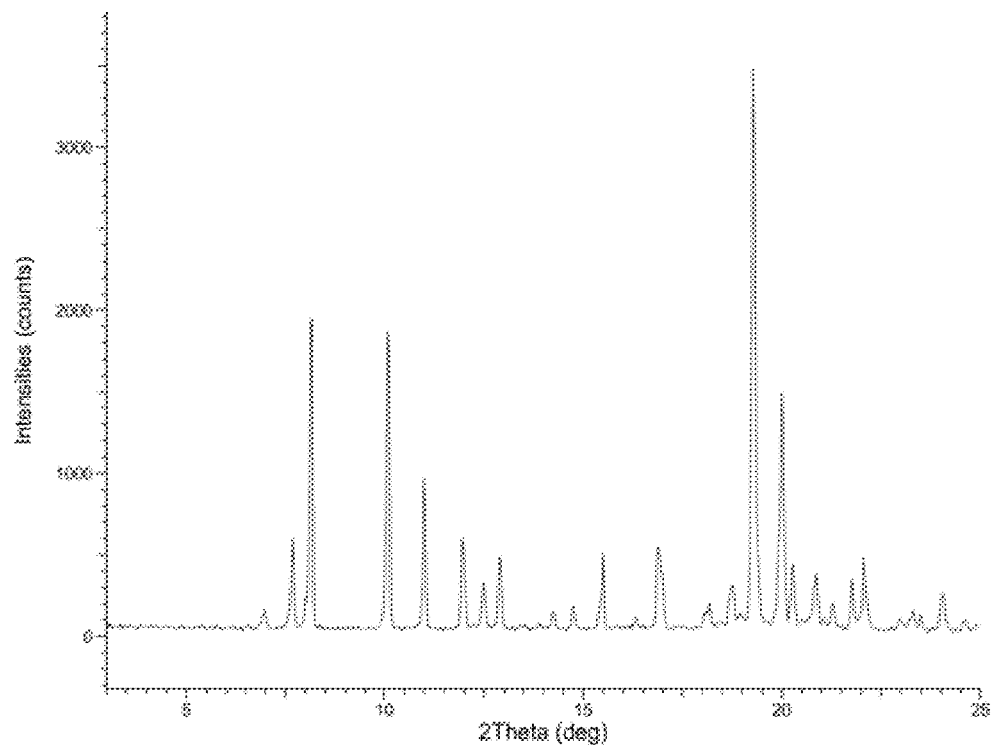
FIG. 9 is a graph of an analysis result of powder X-ray diffraction of the Compound (1).
Figure 10:
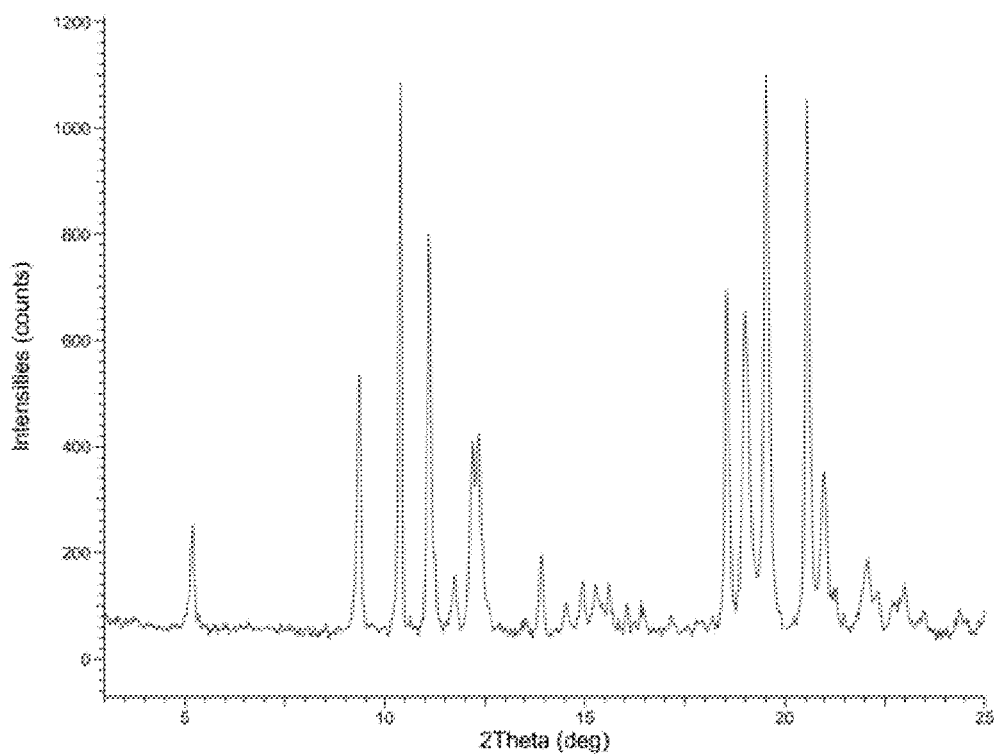
FIG. 10 is a graph of an analysis result of powder X-ray diffraction of the Compound (1).
Figure 11:
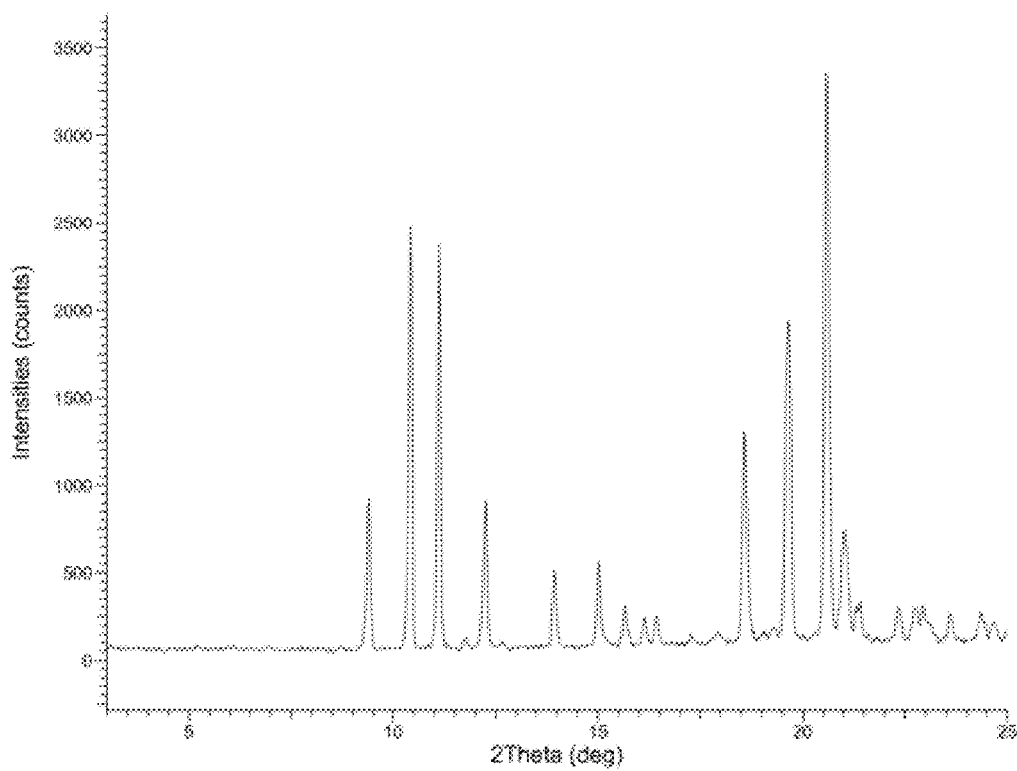
FIG. 11 is a graph of an analysis result of powder X-ray diffraction of the Compound (1).

In a nitrogen atmosphere, 6-cyano-2-[1-[4-ethyl-3-(4-morpholino-1-piperidyl)phenyl]-1-methyl-ethyl]-1H-indole-3-carboxylic acid (VIIIa, 50 g, 100 mmol) was suspended in acetone (500 mL), to which N,N'-diisopropylcarbodiimide (25.2 g, 200 mmol), and diisopropylethylamine (12.9 g, 100 mmol) were added, and the reaction temperature was heated to 55° C. or higher. The liquid was stirred at the same temperature for 4 hours, and thereafter the reaction temperature was cooled to 40° C. The crystals precipitated at this stage exhibited the pattern shown in FIG. 8. Methanol (450 mL) was dropped into the reaction mixture over 30 min, and the mixture was stirred at the same temperature for 30 min. The crystals precipitated at this stage exhibited the pattern shown in FIG. 9. Water (200 mL) was added to the suspension over 30 min, and the suspension was stirred at the same temperature for another 1 hour. The crystals precipitated at this stage exhibited the pattern shown in FIG. 10. The formed crystals were filtrated and collected as a wet powder, and then the wet powder was washed with a mixed solution of methanol and water (methanol:water=12:5, total 425 mL). The wet powder obtained at this stage showed the pattern shown in FIG. 11. The wet powder was dried under a reduced pressure at 50° C. to yield 9-ethyl-6,6-dimethyl-8-[4-(morpholin-4-yl)piperidin-1-yl]-11-oxo-6,11-dihydro-5H-benzo[b]carbazole-3-carbonitrile (Compound (1), 42.734 g) (Yield: 89%).

Figure 12:
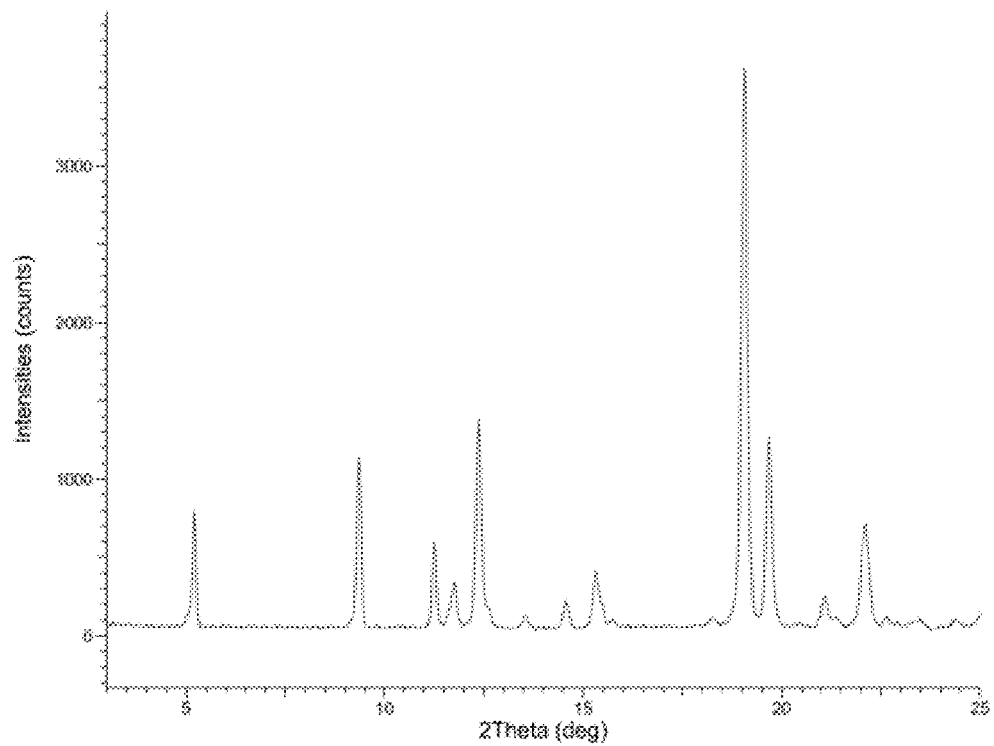
FIG. 12 is a graph of an analysis result of powder X-ray diffraction of the Compound (1).

HPLC purity: 99.85%
Moisture content: 3.7%
Powder X-ray diffraction analysis: Compound (1) obtained by the above method exhibited a pattern as shown in FIG. 12.

B. Manufacturing Method Using Diethyl Chlorophosphate (1)

In a nitrogen atmosphere, 6-cyano-2-[1-[4-ethyl-3-(4-morpholino-1-piperidyl)phenyl]-1-methyl-ethyl]-1H-indole-3-carboxylic acid (VIIIa, 1.0 g, 2.0 mmol) was suspended in THF (20 mL), to which diethyl chlorophosphate (1.155 mL, 8.0 mmol), and diisopropylethylamine (2.4 mL, 14.0 mmol) were added, and the reaction temperature was heated to 68° C. The reaction mixture was stirred at the same temperature for 2 hours, and the reaction temperature was cooled to 40° C. After methanol (7.5 mL) was added to the obtained reaction mixture, the reaction temperature o was cooled to 35° C. Water (12.5 mL) was added to the suspension over 1 hour, and the reaction mixture was stirred for 1 hour at 30° C. of reaction temperature. The obtained solid was filtrated and collected as a wet powder, and then washed with a mixed solution of methanol and water (methanol:water=5:8.7, total 13.7 mL). The wet powder was dried under a reduced pressure at 50° C. to yield 9-ethyl-6,6-dimethyl-8-[4-(morpholin-4-yl)piperidin-1-yl]-11-oxo-6,11-dihydro-5H-benzo[b]carbazole-3-carbonitrile (Compound (1), 0.7225 g) (Yield: 75%).
HPLC purity: 99.87%
Moisture content: 3.8%

C. Manufacturing Method Using Diethyl Chlorophosphate (2)

In a nitrogen atmosphere, 6-cyano-2-[1-[4-ethyl-3-(4-morpholino-1-piperidyl)phenyl]-1-methyl-ethyl]-1H-indole-3-carboxylic acid (VIIIa, 1.0 g, 2.0 mmol) was suspended in acetonitrile (20 mL), to which diethyl chlorophosphate (1.15 mL, 8.0 mmol), and diisopropylethylamine (2.4 mL, 14.0 mmol) were added, and the reaction temperature was heated to 69° C. The reaction mixture was stirred at the same temperature for 2 hours, and the reaction temperature o was cooled to 40° C. Thereafter, methanol (7.5 mL) was added thereto, and then the reaction temperature was cooled to 35° C. Water (12.5 mL) was added to the obtained suspension over 1 hour, and the suspension was stirred for 1 hour at 30° C. of reaction temperature. The obtained solid was filtrated and collected as a wet powder, and then washed with a mixed solution of methanol and water (methanol:water=5:8.7, total 13.7 mL). The wet powder was dried under a reduced pressure at 50° C. to yield 9-ethyl-6,6-dimethyl-8-[4-(morpholin-4-yl)piperidin-1-yl]-11-oxo-6,11-dihydro-5H-benzo[b]carbazole-3-carbonitrile (Compound (1), 0.8107 g) (Yield: 84%).
HPLC purity: 99.5%
Moisture content: 3.8%

D. Manufacturing Method Using Acetic Anhydride (1)

In a nitrogen atmosphere, 6-cyano-2-[1-[4-ethyl-3-(4-morpholino-1-piperidyl)phenyl]-1-methyl-ethyl]-1H-indole-3-carboxylic acid (VIIIa, 1.0 g, 2.0 mmol) was suspended in 2-methyltetrahydrofuran (15 mL), to which acetic anhydride (0.75 mL, 8.0 mmol), and diisopropylethylamine (2.4 mL, 14.0 mmol) were added, and the reaction temperature was heated to 80° C. The reaction mixture was stirred at the same temperature for 6 hours, and the reaction temperature was cooled to 40° C. Thereafter, methanol (4.5 mL) was added thereto, then the reaction temperature was cooled to 35° C. Water (4.5 mL) was added to the obtained suspension over 0.5 hours, and the suspension was stirred for 1 hour at 10° C. or less of reaction temperature. The obtained solid was filtrated and collected as a wet powder, and then washed with a mixed solution of methanol and water (methanol:water=5:8.7, total 13.7 mL). The wet powder was dried under a reduced pressure at 40° C. to yield 9-ethyl-6,6-dimethyl-8-[4-(morpholin-4-yl)piperidin-1-yl]-11-oxo-6,11-dihydro-(Compound (1), 0.673 g) (Yield: 70%).
HPLC purity: 99.77%

E. Manufacturing Method Using Acetic Anhydride (2)

The same operation was performed using N,N-dimethylacetamide as a solvent instead of 2-methyltetrahydrofuran used in D, to obtain Compound (1) (Yield: 85%).
HPLC purity: 99.8%

Example 4

Comparison in Selectivity and Yield of Cyclization Reaction Among Reagent and Solvent Types Using the combination of a reagent and a solvent shown in Table 1, and carrying out the method described in Example 3, the production ratio of the objective substance (Compound (I)) to Impurity (Y) was measured. The production ratio of the objective substance (Compound (I)) to Impurity (Y) (selectivity of cyclization reaction) was determined using a LC-10 system manufactured by Shimadzu Corporation, and based on the peak areas from an HPLC analysis of a reaction mixture using a SunFire column (4.6 mm ID×50 mm). The HPLC analysis was performed using a linear gradient method using a 0.05% aqueous solution of trifluoroacetic acid (A), and a 0.05% acetonitrile solution of trifluoroacetic acid (B) (Table 3, flow rate 1 mL/min), and the calculation was conducted based on absorption peak areas at 230 nm. The retention time for each compound was about 6.8 min for the objective substance (Compound (1)), and about 3.8 min for Impurity (Y).

Comparison in selectivity and yield of cyclization reaction among respective reagent and solvent types is shown in Table 2.

In this regard, Impurity (Y) is the following compound, which is cyclized by a Friedel-Crafts type reaction at a substitution position different from that of the objective substance (Compound (1)).

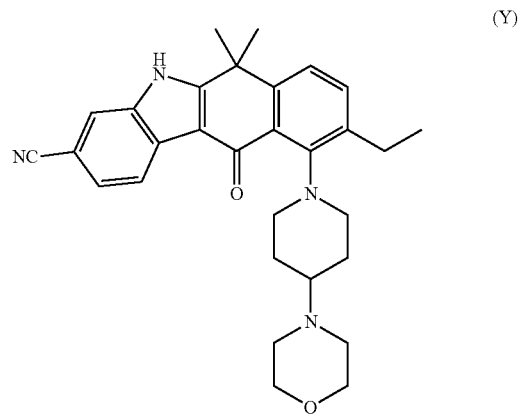 [SMILES: CCc1ccc2c(c1N1CCC(N3CCOCC3)CC1)C(=O)c1c([nH]c3cc(C#N)ccc13)C2(C)C]

(Y)

TABLE 2

| Solvent | Reagent | Selectivity of objective substance (Compound (1))/Impurity (Y) | Yield of objective substance |
|---|---|---|---|
| DMA | Acetic anhydride | 47 | 85% |
| 2-MeTHF | Acetic anhydride | 14 | 70% |
| THF | Diethyl chlorophosphate | 490 | 75% |
| Acetonitrile | Diethyl chlorophosphate | 300 or more | 84% |
| Acetone | DIC | 200 | 89% |

From the above results, it has become clear that regarding the selectivity of the objective substance, the reaction selectivity is significantly improved by using diethyl chlorophosphate, or N,N'-diisopropylcarbodiimide (DIC) in place of acetic anhydride. Further it has become clear that the yield of the objective substance is greatly improved by using a combination of N,N'-diisopropyl carbodiimide and acetone.

TABLE 3

| Time (min) | A rate | B rate |
|---|---|---|
| 0 | 85% | 15% |
| 16-17 | 0% | 100% |

A rate: Percentage of the 0.05% aqueous solution of trifluoroacetic acid solution based on the total flow rate B rate: Percentage of the 0.05% acetonitrile solution of trifluoroacetic acid solution based on the total flow rate

Example 5

Production of 9-ethyl-6,6-dimethyl-8-[4-(morpholin-4-yl)piperidin-1-yl]-11-oxo-6,11-dihydro-5H-benzo[b]carbazole-3-carbonitrile hydrochloride (hydrochloride of the Compound (1)) [Step 6]

In a nitrogen atmosphere, 2-butanone (350 mL), water (122.5 mL), and acetic acid (105 mL) were added to 9-ethyl-6,6-dimethyl-8-[4-(morpholin-4-yl)piperidin-1-yl]-11-oxo-6,11-dihydro-5H-benzo[b]carbazole-3-carbonitrile (Compound (1), 35 g, 72.5 mmol), and dissolution was carried out at an outside temperature of 35° C. This solution was dropped into a mixture liquid of a 2 mol/L hydrochloric acid (70 mL) and ethanol (350 mL) heated to an inside temperature of 60° C., while maintaining the mixture liquid temperature at 60° C. Furthermore, a mixed solvent of 2-butanone (70 mL), water (24.5 mL), and acetic acid (21 mL) was dropped while maintaining the mixture liquid temperature at 60° C. The reaction mixture was stirred at the same temperature for 1 hour, and then cooled down to the inside temperature of the reaction mixture of 20° C. over 2 hours. The reaction mixture was stirred for 30 min, and the formed solid was collected by filtration, and the obtained wet powder was washed with ethanol (350 mL). The wet powder was dried under a reduced pressure at an outside temperature of 40° C., to yield 9-ethyl-6,6-dimethyl-8-[4-(morpholin-4-yl)piperidin-1-yl]-11-oxo-6,11-dihydro-5H-benzo[b]carbazole-3-carbonitrile hydrochloride (Compound (1) hydrochloride, 31.15 g) (Yield: 82.8%).

HPLC purity: 99.95%

Impurity (X) Formed in the Process of Manufacturing Compound (1) Hydrochloride from Compound Ia 3-Cyano-9-ethyl-6,6-dimethyl-8-(4-morpholino-1-piperidyl)-11-oxo-5H-benzo[b]carbazole-2-sulfonic acid

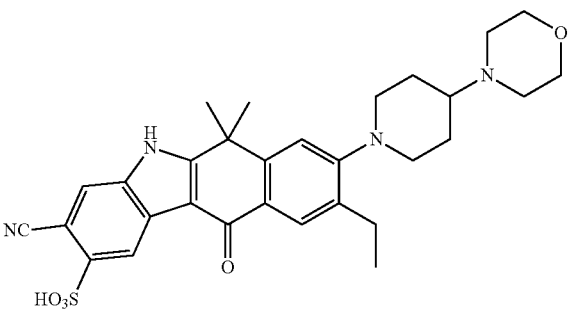 [SMILES: CCc1cc2c(cc1N1CCC(N3CCOCC3)CC1)C(C)(C)c1[nH]c3cc(C#N)c(S(=O)(=O)O)cc3c1C2=O]

$^1$H NMR (500 MHz, dimethylsulfoxide-$d_6$) δ 1.28 (3H, t, J=7.2 Hz), 1.53-1.69 (2H, m) 1.75 (6H, s), 1.92 (2H, d, J=11.5 Hz), 2.28-2.39 (1H, m), 2.50-2.82 (8H, m), 3.22 (2H, d, J=11.5 Hz), 3.57-3.64 (4H, m), 7.33 (1H, s), 7.86 (1H, s), 8.04 (1H, s), 8.70 (1H, s), 12.65 (1H, brs)

According to the present invention, a method for manufacturing Compound (1) in a high yield can be provided, in which a solvent of concern with respect to environmental load and workers' health is not used, and which is constituted with a process exhibiting high robustness and long durability in manufacturing a drug owing to easy control of impurities.

The invention claimed is:

1. A method for manufacturing Compound (1):

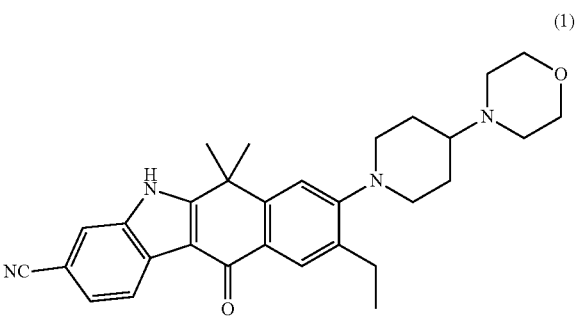 [SMILES: CCc1cc2c(cc1N1CCC(N3CCOCC3)CC1)C(C)(C)c1[nH]c3cc(C#N)ccc3c1C2=O]

or a pharmaceutically acceptable salt thereof, the method comprising a step of manufacturing a compound represented by Formula IXa:

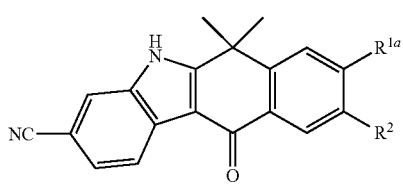
(IXa)

or a pharmaceutically acceptable salt thereof, by treating a compound represented by Formula VIIIb:

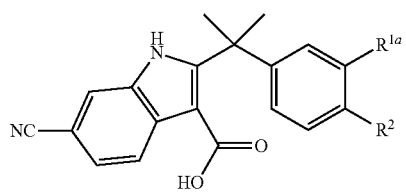
(VIIIb)

wherein $R^{1a}$ represents 4-(morpholin-4-yl)piperidin-1-yl group, iodo group, or bromo group; and $R^2$ represents an ethyl group, with a condensing agent selected from N,N'-diisopropylcarbodiimide and diethyl chlorophosphate in a solvent selected from dichloromethane, 1,4-dioxane, 2-methyltetrahydrofuran, 2-butanone, tert-butyl methyl ether, ethyl acetate, isopropyl acetate, dimethyl sulfoxide, tetrahydrofuran, acetone, and acetonitrile.

2. The method according to claim 1, further comprising:

(1) Step 1a: a step of reacting a compound represented by Formula I:

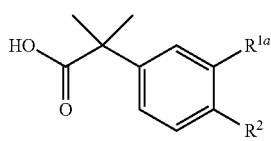
(I)

wherein $R^{1a}$ represents a 4-(morpholin-4-yl)piperidin-1-yl group, iodo or bromo group and $R^2$ represents an ethyl group, in the presence of an acid to produce a compound represented by Formula II:

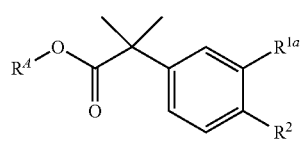
(II)

wherein $R^{1a}$ and $R^2$ are as defined above; and R A represents a $C_1$-$C_6$ alkyl group;

(2) a step of reacting the compound represented by Formula II with a base and $AcOR^B$ to produce a compound represented by Formula III:

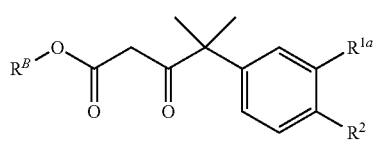
(III)

wherein $R^B$ represents a $C_1$-$C_6$ alkyl group;

(3) a step of reacting the compound represented by Formula III with a compound represented by Formula IV and a base:

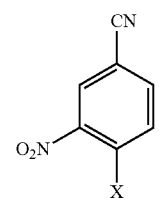
(IV)

wherein X represents a leaving group,
to produce a compound represented by Formula V:

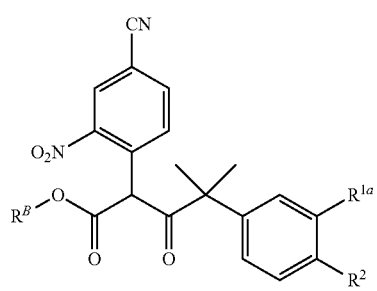
(V)

wherein $R^{1a}$, $R^2$, and $R^B$ are as defined above; and any one of following steps (4) and (5):

(4) a step of reacting the compound represented by Formula V where $R^{1a}$ represents a 4-(morpholin-4-yl) piperidin-1-yl group with a reducing agent to produce a compound represented by
Formula VII:

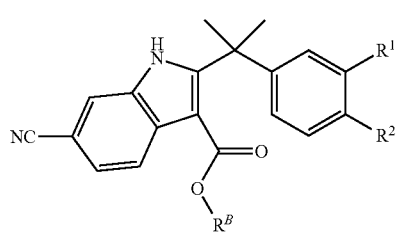
(VII)

wherein $R^1$ represents a 4-(morpholin-4-yl)piperidin-1-yl group and $R^2$ and $R^B$ are as defined above;

(5) a step of reacting the compound represented by Formula V where $R^{1a}$ represents an iodo or bromo group with a reducing agent to produce a compound represented by Formula (VI):

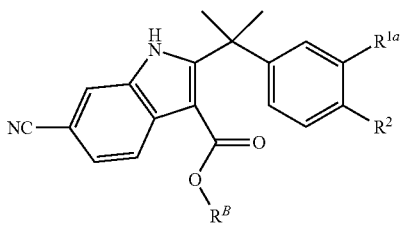

(VI)

wherein R¹ᵃ represents an iodo or bromo group, R² and R^B are as defined above, and reacting the compound represented by Formula (VI) with 4-(4-piperidinyl)morpholine in the presence of a palladium catalyst to produce a compound represented by Formula VII:

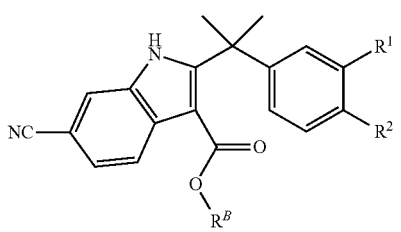

(VII)

wherein R¹ represents 4-(morpholin-4-yl)piperidin-1-yl group and R² and R^B are as defined above, or a pharmaceutically acceptable salt thereof, and (6) a step of reacting the compound represented by Formula VII with an acid to produce a compound represented by Formula VIII:

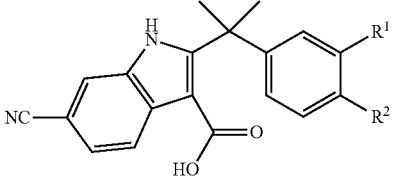

(VIII)

wherein R¹ and R² are as defined above.

3. The method according to claim 1, wherein the solvent is selected from tetrahydrofuran, acetone, and acetonitrile.

4. The method according to claim 2, wherein the acid in (1) is from acetyl chloride and an alcohol.

5. The method according to claim 2, wherein the base in (2) is lithium hexamethyldisilazide, or sodium hexamethyldisilazide.

6. The method according to claim 2, wherein the R^B in (2) is a tert-butyl group.

7. The method according to claim 2, wherein the leaving group in (3) is a fluoro group or a chloro group.

8. The method according to claim 2, wherein the base in (3) is sodium hydroxide, potassium phosphate, potassium carbonate, or cesium carbonate, and the reaction solvent is tetrahydrofuran.

9. The method according to claim 2, wherein the reducing agent in (4) is sodium hydrosulfite.

10. The method according to claim 2, wherein the palladium catalyst in (5) is a combination of II-allylpalladium chloride dimer and 2',6'-dimethoxy-2-(dicyclohexylphosphino)biphenyl (S-Phos), PEPPSI-IPent, or S-Phos Pd(crotyl)Cl; and the reaction in the step 3 is carried out in a mixed solvent of tetrahydrofuran and 1,3-dimethyl-2-imidazolidinone.

11. The method according to claim 2, wherein the acid in (6) is from trimethylsilyl chloride and 2,2,2-trifluoroethanol.

12. The method according to claim 1, wherein the Compound (1) is a hydrochloride salt thereof.

13. The method according to claim 1, wherein the Compound (1) is a hydrochloride salt thereof, and wherein the method produces a compound represented by Formula X is at 0.08% or less based on the weight of the hydrochloride salt of the Compound (1)

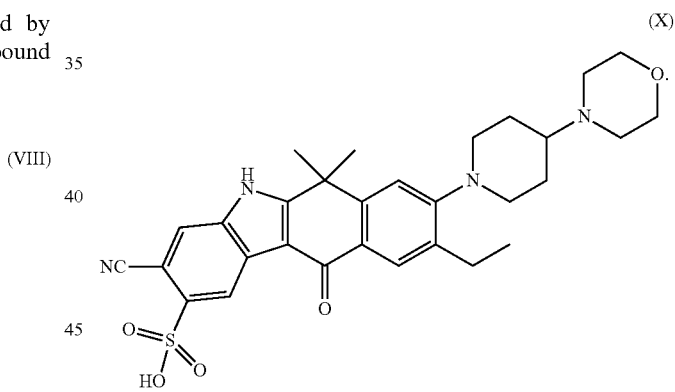

(X)

* * * * *